US008163505B2

(12) United States Patent
Shi et al.

(10) Patent No.: US 8,163,505 B2
(45) Date of Patent: Apr. 24, 2012

(54) METHODS USING PBK1 FOR IDENTIFYING AGENTS THAT TREAT METABOLIC DISORDERS

(75) Inventors: Yuguang Shi, Hershey, PA (US); Guangming Ye, Hershey, PA (US)

(73) Assignee: The Penn State Research Foundation, University Park, PA (US)

( * ) Notice: Subject to any disclaimer, the term of this patent is extended or adjusted under 35 U.S.C. 154(b) by 595 days.

(21) Appl. No.: 12/154,296

(22) Filed: May 22, 2008

(65) Prior Publication Data

US 2010/0146642 A1 Jun. 10, 2010

Related U.S. Application Data

(60) Provisional application No. 60/939,462, filed on May 22, 2007.

(51) Int. Cl.
*G01N 33/53* (2006.01)
*G01N 33/567* (2006.01)

(52) U.S. Cl. ...................................... 435/7.2; 435/7.21
(58) Field of Classification Search .................. None
See application file for complete search history.

(56) References Cited

U.S. PATENT DOCUMENTS

| | | | | |
|---|---|---|---|---|
| 6,124,125 | A | 9/2000 | Kemp et al. | |
| 6,455,292 | B1 * | 9/2002 | Shu et al. ...................... | 435/194 |
| 7,098,220 | B2 | 8/2006 | Rault et al. | |
| 7,119,205 | B2 | 10/2006 | Iyengar et al. | |
| 7,141,240 | B2 * | 11/2006 | Perfetti et al. ............. | 424/93.21 |
| 7,208,305 | B2 | 4/2007 | Hjalm | |
| 7,320,806 | B2 | 1/2008 | Miljkovic et al. | |

FOREIGN PATENT DOCUMENTS

WO WO-2005010174 2/2005

OTHER PUBLICATIONS

Sabater, L., M. Gomez-Choco, A. Saiz, F. Graus. "BR/serine/threonine kinase 2: A new autoantigen in paraneoplastic limbic encephalitis." *Journal of Neuroimmunology* 2005, vol. 170, pp. 186-190.
Kishi, M., Y.A. Pan, J.G. Crump, J.R. Sanes. "Mammalian SAD Kinases Are Required for Neuronal Polarization." *Science* 2005, vol. 307, pp. 929-932.
Nevins, A.K. and D.C. Thurmond. "A Direct Interaction between Cdc42 and Vesicle-associated Membrane Protein 2 Regulates SNARE-dependent Insulin Exocytosis." *The Journal of Biological Chemistry* 2005, vol. 280, No. 3, pp. 1944-1952.
Kashima, Y., T. Miki, T. Shibasaki, N. Ozaki, M. Miyazaki, H. Yano, and S. Seino. "Critical Role of cAMP-GEFII Rim2 Complex in Incretin-potentiated Insulin Secretion." *The Journal of Biological Chemistry* 2001, vol. 276, No. 49, pp. 46046-46053.
Wang, Y., S. Sugita, and T.C. Sudhof. "The RIM/NIM Family of Neuronal $C_2$ Domain Proteins." *The Journal of Biological Chemistry* 2000, vol. 275, No. 26, pp. 20033-20044.
Drucker, D.J. "The biology of incretin hormones." *Cell Metabolism* 2006, vol. 3, pp. 153-165.
Miura, K., H. Masuzaki, T. Ishimuru, N. Niikawa, and Y. Jinno. "A Hha I/ Bst UI polymorphism in a novel gene at human chromosome 11p15.5." *Journal of Human Genetics* 1998, vol. 43, No. 4, pp. 283-284.
Oak, S., L.K. Gilliam, M. Landin-Olsson, C. Torn, I. Kockum, C.R. Pennington, M.J. Rowley, M.R. Christie, J.P. Banga, C.S. Hampe. "The lack of anti-idiotypic antibodies to glutamate decarboxylase, defines type 1 diabetes." *Proceedings of the National Academy of Sciences USA* 2008, vol. 105, No. 14, pp. 5471-5476.
Rhodes, C. "Type 2 Diabetes—a Matter of β-Cell Life and Death?" *Science* 2005, vol. 307, No. 5708, pp. 380-384.
Stanchi, F., E. Bertocco, S. Toppo, R. Dioguardi, B. Simionati, N. Cannata, R. Zimbello, G. Lanfranchi, G. Valle. "Characterization of 16 novel human genes showing high similarity to yeast sequences." *Yeast* 2001, vol. 18, No. 1, pp. 69-80.
Hui, H. et al., Transfection of pancreatic-derivatived b-cells with a minigene encoding for human glucagon-like peptide-1 regulates glucose-dependent insulin synthesis and secretion, *Endocrinology*, 143:3529-3539, 2002.
GenBank Accession No. EAX02436, "BR serine/threonine kinase 2, isoform CRA_a [*Homo sapiens*]", Dec. 18, 2006. See http://www.ncbi.nlm.nih.gov/entrez/viewer.fcgi?db=protein&id+119622841.
GenBank Accession No. AF533876, "*Homo sapiens* putative serine/threonine protein kinase variant A mRNA, complete cds", Jul. 24, 2003. See http://www.ncbi.nlm.nih.gov/entrez/viewer.fcgi?db=nuccore&id=33187737.
Sabater, L. et al., BR serine/threonine kinase 2: A new autoantigen in paraneoplastic limbic encephalitis, *Journal of Neuroimmunology*, 170:186-190, 2005.
Guo, Z. et al., BRSK2 is activated by cyclic AMP-dependent protein kinase A through phosphorylation at Thr260, *Biochemical and Biophysical Research Communications*, 347:867-871, 2006.

* cited by examiner

*Primary Examiner* — Robert Landsman
(74) *Attorney, Agent, or Firm* — Gifford, Krass, Sprinkle, Anderson & Citkowski, P.C.

(57) ABSTRACT

The invention relates to compositions comprising, and methods utilizing PBK1 protein and DNA, including a method of detecting type 1 diabetes; a mammalian pancreas-derived cell comprising a recombinant nucleic acid encoding a PBK1 protein; a method of identifying a PBK1 modulator; a pharmaceutical composition for treatment of type 2 diabetes in a subject; a method of screening for an agent that treats a metabolic disease; delivery of PBK-1 DNA to a subject to stimulate pancreatic beta cell differentiation and/or regeneration; a method for stimulating cell differentiation and/or regeneration in a pancreatic beta cell; usage of transgenic mice with targeted deletion or overexpression of the PBK-1 gene to test efficacy and specificity of PBK-1 modulator compounds.

11 Claims, 6 Drawing Sheets

METHODS USING PBK1 FOR IDENTIFYING AGENTS THAT TREAT METABOLIC DISORDERS

This application claims the benefit of priority from U.S. provisional application 60/939,462, filed May 22, 2007, the entire contents of which is hereby incorporated herein by reference.

REFERENCE TO SEQUENCE LISTING APPENDIX

Amino acid and nucleic acid sequences are shown in appended pages marked "Appendix" and are also being submitted on the accompanying compact disc; said amino acid and nucleic acid sequences are considered part of this application and are incorporated herein by reference in their entirety.

FIELD OF THE INVENTION

The invention relates to compositions comprising, and methods utilizing PBK1 (pancreas brain kinase 1) protein and DNA.

BACKGROUND OF THE INVENTION

It was estimated that approximately 150 million people worldwide had type 2 diabetes (T2D) in the year 2000, with the prediction that this number could double to 300 million by 2025 (1). T2D is characterized by insulin resistance in peripheral tissues and deficient β-cell insulin-secretory response to glucose. Glucose-sensing by pancreatic β-cell plays an important role in regulating glucose homeostasis and onset of T2D. Normal pancreatic β-cells are able to sense minor changes in blood glucose levels, and promptly respond to such changes by adjusting insulin secretion rates to maintain normoglycemia (2). In patients with insulin resistance, the pancreatic β-cells have to secret higher levels of insulin as a compensatory response to insulin resistance in order to maintain normoglycemia, resulting in hyperinsulinemia. Consequently, T2D develops only in subjects that are unable to sustain this β-cell compensatory response (3, 4). This is supported by results from longitudinal studies of subjects that develop T2D. These patients show a rise in insulin levels in the normoglycemic and prediabetes phases, followed by a decline in insulin secretion when β cells loss their ability to sense glucose, resulting pancreatic β cell failure and onset of diabetes (5). A longitudinal study in Pima Indians also confirmed that β-cell dysfunction was the major determinant of progression from normoglycemia to diabetes (6). Furthermore, the natural history of T2D entails progressive deterioration in β-cell function (7) and loss of β cell mass due to apoptosis (8, 9).

Current treatment options for type 2 diabetes include insulin, sulfonylureas, glitinides, acarbose, metformin, thiazolidinediones. These drugs lower blood glucose through diverse mechanisms of action. However, many of the drugs cannot prevent β-cell death or re-establish β-cell mass, and most of the oral hypoglycemic agents lose their efficacy over time, resulting in progressive deterioration in β-cell function and loss of glycemic control. Moreover, sulfonylurea therapy has been shown to induce apoptosis in rodent β-cells (10) or cultured human islets (11), thus likely exacerbating β-cell loss in T2D patients. Consequently, there has been intense interest in the development of therapeutic agents that preserve or restore functional β-cell mass (12). Several agents with the potential to inhibit β-cell apoptosis and/or increase β-cell mass have been identified in preclinical studies (12). One of the agents, a GLP-1 analogue, commercially known as Byetta (exenatide), has been shown to lower blood glucose level by improving β-cell function (β-15). Byetta is a peptide derived from the venom of the Gila monster, a poisonous lizard. Treatment of β-cell with Byetta has been shown to improve β-cell glucose sensing concurrent with preservation of β-cell mass and stimulation of β-cell regeneration (16). However, Byetta must be administered by injection twice daily, and long term usage of the drug has been associated with development of anti-exenatide antibodies in diabetic subjects. Additionally, the drug slows gastric emptying, and causes gastrointestinal discomfort.

Thus, there is a continuing need for compositions and methods for detection and treatment of diabetes in a subject. Further, development, of an oral antidiabetic drug that can improve glucose sensing by pancreatic β-cells is required for treatment of type 2 diabetes.

SUMMARY OF THE INVENTION

Figure 1:
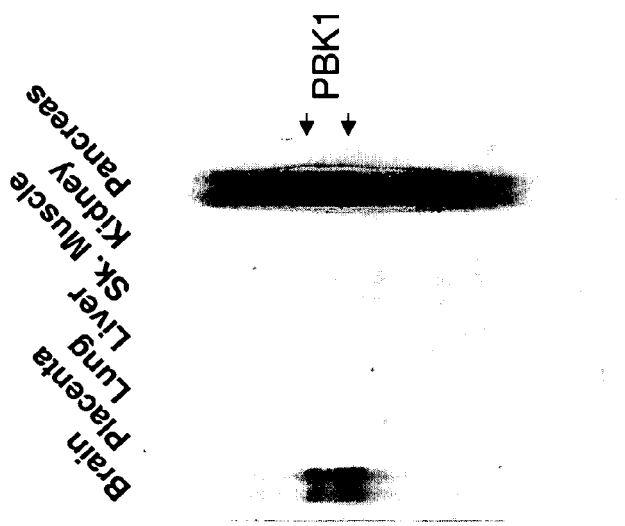
FIG. 1 depicts a northern blot that indicates that PBK1 mRNA is most abundantly expressed in human pancreas.

The invention relates to compositions comprising-, and methods utilizing PBK1 protein and DNA.

In one aspect, the invention provides a method of detecting type 1 diabetes in a patient, comprising: reacting a patient sample with a PBK1 protein or a fragment thereof under conditions that promote antibody-antigen binding; and detecting the presence of an autoantibody in said sample.

In one embodiment of the present invention, the PBK1 protein is immobilized on a solid support. In another embodiment, the patient sample is selected from the group consisting of: blood, serum, plasma, and a biopsy tissue. In another, the detecting of the autoantibody comprises reacting the autoantibody with an antibody having a detectable label.

In another aspect, the invention provides a mammalian pancreas-derived cell comprising a recombinant nucleic acid encoding a PBK1 protein.

In one embodiment of the present invention, the cell is a cell of a mammalian pancreas-derived cell line. In another embodiment, the cell is a Min6 cell transfected with a recombinant nucleic acid encoding a PBK1 protein.

In another aspect, the invention provides a method of detecting a PBK1 modulator, comprising: contacting PBK1 with a compound; and detecting a change in PBK1 activity, the change in PBK1 activity indicative that the compound is a PBK1 modulator.

In a related aspect, the invention encompasses a pharmaceutical composition for treatment of type 2 diabetes in a subject, the composition comprising a modulator of PBK1.

In a further related aspect, the invention provides a method of identifying a PBK1 modulator, comprising one or more of: a) contacting a PBK1 protein with a test agent under conditions that promote kinase activity of said PBK1 protein, and detecting an increase in the kinase activity; and b) contacting a cell that expresses a PBK1 protein with a test agent under conditions that promote glucose-stimulated insulin secretion from said cell, and detecting an increase in the glucose-stimulated insulin secretion from the cell; wherein said increase in a) or b) each indicates that the test agent is a PBK1 modulator.

In one embodiment of the present invention, the method further comprises determining that the increase in the glucose-stimulated insulin secretion comprises potentiation of secretagogue-stimulated insulin secretion from a cell that expresses a PBK1 protein. In another embodiment, the cell is a mammalian pancreas-derived cell. In another, the cell is a MIN6 cell. In another, the cell contains a recombinant nucleic acid encoding a PBK1 protein.

In another aspect, the invention provides a method of screening for an agent that treats a metabolic disease, said method comprising one or more of:

a) contacting a PBK1 protein with a test agent under conditions that promote binding of said test agent to said PBK1 protein, and detecting binding of said test agent to said PBK protein;

b) contacting a PBK1 protein with a test agent under conditions that promote kinase activity of said PBK1 protein, and detecting an increase in the kinase activity; and c) contacting a cell that expresses a PBK protein with a test agent under conditions that promote glucose-stimulated insulin secretion from said cell, and detecting an increase in the glucose-stimulated insulin secretion from the cell; wherein said disorder is selected from diabetes, type 2 diabetes, obesity, and diabetic retinopathy.

In one embodiment of the present invention, the screening method further comprises designating said test agent as an agent that treats said disease. In another embodiment, the screening method further comprises designating said test agent as an agent that treats type 2 diabetes.

In another embodiment, the PBK1 protein is selected from a protein having a polypeptide sequence that has at least 73%, 75%, 80%, 85%, 90%, 91%, 92%, 93%, 94%, 95%, 96%, 97%, 98%, or 99% identity to the protein having a polypeptide sequence set forth in SEQ ID NO: 2.

In another embodiment, the PBK1 protein is selected from a protein having a polypeptide sequence set forth in SEQ ID NO: 2 or SEQ ID NO: 6.

In another embodiment, step a) is performed prior to step c). In another, step b) is performed prior to step c). In another, step a) is performed prior to b), and step b) is performed prior to step c).

In another embodiment, the screening method further comprises determining that the increase in the glucose-stimulated insulin secretion comprises potentiation of secretagogue-stimulated insulin secretion from a cell that expresses a PBK1 protein. In another, the cell is a mammalian pancreas-derived cell. In another, the cell is a MIN6 cell. In another, the cell contains a recombinant nucleic acid encoding a PBK1 protein.

In another aspect, the invention comprehends delivery of PBK-1 DNA to a subject to stimulate pancreatic beta cell differentiation and/or regeneration.

In a related aspect, the invention provides a method for stimulating cell differentiation and/or regeneration in a pancreatic beta cell comprising delivering PBK-1 DNA to said cell. In one embodiment of the present invention, the DNA is operably linked to a promoter that drives expression of said DNA in said cell. In one embodiment, the promoter is an adenoviral promoter, retroviral promoter, or any promoter that can direct expression of PBK1 expression in mammalian cells, tissues, or living body.

In another aspect, the invention comprehends the usage of transgenic mice with targeted deletion or overexpression of the PBK-1 gene to test efficacy and specificity of PBK-1 modulator compounds.

In a related aspect, the invention provides a method for in vivo screening for an agent that treats diabetes, said method comprising: a) subjecting a mammal comprising a PBK1 knockout genome to a diet that promotes diabetes; b) treating said mammal with a test agent; c) determining blood glucose level of said mammal; and d) determining whether said mammal is glucose tolerant. In one embodiment of the present invention, the animal is heterozygous for the PBK1 knockout. In another, the animal is homozygous for the PBK1 knockout.

DETAILED DESCRIPTION OF THE INVENTION

PBK1 (pancreas brain kinase), is shown herein to play a key role in regulating glucose-sensing. Overexpression of PBK1 in MIN6 cells greatly improves their glucose-sensing by more than three fold, much greater than that by GLP-1. Moreover, data detailed herein show that PBK1 also enhances insulin secretion stimulated by GLP-1 and other insulin secretagogues by improving the stimulus-secretion coupling function of β-cells. It is further demonstrated that PBK1 is a "master" regulator of the networks that regulate glucose-sensing, since PBK1 is associated with both synaptic-like microvesicles and insulin secretion granules. PBK1 is predominantly expressed in brain and pancreas, thus eliminating or reducing potential problems of functionally related side effects of an oral antidiabetic compound.

Various embodiments described herein refer to type 1 diabetes and/or type 2 diabetes. For the purposes of the invention described herein these references to the types of diabetes are made consistently with the 1997 recommendations of the American Diabetes Association expert committee for universal adoption of simplified terminology, with which recommendations the National Institute of Diabetic and Digestive and Kidney Diseases (NIDDK) agreed. Accordingly, for the purposes of the invention described herein, type 1 diabetes encompasses art-recognized references to type I diabetes, juvenile diabetes, insulin-dependent diabetes mellitus, and/or IDDM; and type 2 diabetes encompasses art-recognized references to type II diabetes, adult-onset diabetes, noninsulin-dependent diabetes mellitus, and/or NIDDM.

In accordance with the present invention, various techniques and terms, including, but not limited to, conventional molecular biology, microbiology, immunology and recombinant DNA techniques and terms may be used which are known by those of skill in the art. Such techniques and terms are described and/or defined in detail in standard references such as Sambrook, et al., Molecular Cloning: A Laboratory Manual, 2nd Ed., Cold Spring Harbor Laboratory Press, Cold Spring Harbor, N.Y., 1989; Ausubel, F. et al., Current Protocols in Molecular Biology, John Wiley & Sons, 1994; Wild, D., The Immunoassay Handbook, 3rd Ed., Elsevier Science, 2005; Gosling, J. P., Immunoassays: A Practical Approach, Practical Approach Series, Oxford University Press, 2005; and Harlow, E. and Lane, D., Antibodies: A Laboratory Manual, Cold Spring Harbor Laboratory Press, 1988; and other references described herein.

PBK1 protein provided in compositions and methods described herein may be isolated from natural sources, such as brain or pancreas of an organism. Alternatively, PBK1 protein may be generated recombinantly, such as be expression using an expression construct, in vitro or in vivo. Nucleic acid sequences encoding PBK1 have been isolated as exemplified by nucleic acid sequences described herein along with amino acid sequences of PBK1. Methods and compositions are not limited to PBK1 having the amino acid sequence described herein in detail. Homologs, including orthologs, of PBK1 may be used. In addition, as will be appreciated by one of skill in the art, due to the degeneracy of the genetic code, more than one nucleic acid will encode an identical protein. Thus, nucleic acids encoding PBK1 or a homolog thereof are not limited to those nucleic acids described herein in detail.

"PBK1 protein" means a protein having at least 73%, 75%, 80%, 85%, 90%, 91%, 92%, 93%, 94%, 95%, 96%, 97%, 98%, 99%, or 100% identity to the protein having a polypeptide sequence set forth in SEQ ID NO: 2, or a protein encoded by a nucleic acid sequence that hybridizes under high stringency hybridization conditions to the nucleic acid set forth in SEQ ID NO: 1 or a complement thereof so long as the protein effects the function described in the particular inventive method comprising use of the protein. For example, in a method of screening of the invention, a protein encoded by a nucleic acid sequence that hybridizes under high stringency hybridization conditions to the nucleic acid set forth in SEQ ID NO: 1 or a complement thereof is operable in the inventive method so long as the protein effects the described binding, kinase activity, or glucose-stimulated insulin secretion.

High stringency hybridization conditions are known to the ordinarily skilled artisan. For instance, high stringency conditions can be achieved by incubating the blot overnight (e.g., at least 12 hours) with a long polynucleotide probe in a hybridization solution containing 7% SDS, 0.5 M $NaPO_4$, pH 7, 1 mM EDTA at 65° C., followed by one or more washes with a 0.1% SDS, 1×SSC solution at 65° C. Whereas high stringency washes can allow for less than 5% mismatch, reduced or low stringency conditions can permit up to 20% nucleotide mismatch.

A fragment of PBK1 protein is any fragment of a PBK1 protein that is operable in the described method utilizing the fragment, as understood by the ordinarily skilled artisan. A fragment of PBK1 protein is operative in any of the inventive methods described herein utilizing a PBK1 protein. For example, in a method of the invention comprising reacting a patient sample with a PBK1 protein or a fragment thereof under conditions that promote antibody-antigen binding, a fragment of the PBK1 will be such understood to be operative, so long as the fragment effects the described antibody-antigen binding. Furthermore, it is understood by the ordinarily skilled artisan that such binding refers to specific binding as determinable by use of appropriate controls to distinguish it from nonspecific binding. Similarly, it is understood by the ordinarily skilled artisan that binding of a test agent or modulator to PBK1 protein refers to specific binding as determinable by use of appropriate controls to distinguish it from nonspecific binding.

"PBK1 DNA" means an isolated DNA molecule having a sequence that has at least 73%, 75%, 80%, 85%, 90%, 91%, 92%, 93%, 94%, 95%, 96%, 97%, 98%, or 99% identity to the DNA sequence set forth in SEQ ID NO: 1, or an isolated DNA molecule having a sequence that hybridizes under high stringency hybridization conditions to the nucleic acid set forth in SEQ ID NO: 1 or a complement thereof, so long as the DNA effects the function described in the particular inventive method comprising use of the DNA. PBK1 DNA includes an isolated DNA molecule that has a sequence set forth in SEQ ID NO: 1, SEQ ID NO: 5, or SEQ ID NO: 18. A fragment of PBK1 DNA is any fragment of a PBK1 protein that is operable in the described method utilizing the fragment, as understood by the ordinarily skilled artisan. A fragment of PBK1 DNA is operative in any of the inventive methods described herein utilizing a PBK1 DNA.

A "test agent" or "modulator" as described in any of the inventive methods provided herein comprehends a compound; small molecule; biochemical; cytokine; biological including protein, peptide, antibody, or fragments thereof.

Conditions that promote binding, kinase activity, or glucose-stimulated insulin secretion as described in any of the inventive methods provided herein are well known in the art; including such conditions described in the references provided herein, and otherwise described or illustrated herein.

Methods of detecting type 1 diabetes are provided according to the present invention which include detecting an autoantibody in a patient sample by reacting the patient sample with a PBK1 protein. Detection of an autoantibody in the sample is indicative of type 1 diabetes in the patient. In particular embodiments, methods of the present invention for detecting type 1 diabetes are advantageously used to screen patients suspected of developing type 1 diabetes or likely to be susceptible to developing type 1 diabetes. For example, an inventive assay is used in a subject having a medical history or genetic background which predisposes the subject to development of type 1 diabetes.

Any of various techniques may be used to detect an autoantibody to PBK1 in a sample obtained from a subject. Standard immunomethods including, but not limited to, ELISA, radioimmunoassay, immunoblotting, immunoprecipitation assay, or immunodiffusion assay, may be used to detect an autoantibody to PBK1 in a sample. Immunomethods are described in detail in standard references such as Wild, D., The Immunoassay Handbook, 3rd Ed., Elsevier Science, 2005; Gosling, J. P., Immunoassays: A Practical Approach, Practical Approach Series, Oxford University Press, 2005; and Harlow, E. and Lane, D., Antibodies: A Laboratory Manual, Cold Spring Harbor Laboratory Press, 1988.

PBK1 protein or its peptide analogues may be immobilized on a solid support for incubation with the patient sample in particular embodiments.

PBK1 protein used in methods of the present invention for detection of type 1 diabetes is full-length PBK1 in particular embodiments. In further embodiments, an antigenic fragment of PBK1 is used. An antigenic fragment of PBK1 is a portion of a PBK1 protein which stimulates an immune response in a subject.

A patient sample is typically a blood, serum, plasma, and/or biopsy tissue sample. A particular biopsy tissue used in a method of the present invention is pancreas biopsy tissue. In addition to detection of type 1 diabetes, methods and compositions for use in treatment of diabetes are provided according to embodiments of the present invention.

In a particular embodiment, a mammalian pancreas-derived cell including a recombinant nucleic acid encoding PBK1 is provided. A mammalian pancreas-derived cell including a recombinant nucleic acid encoding PBK1 may be a primary pancreas cell, such as a pancreatic beta cell or a cell of a mammalian pancreas-derived cell line. In particular embodiments a cell of a mammalian pancreas-derived cell line is a Min6 cell. Further embodiments include any human pancreatic beta cell line including a recombinant nucleic acid encoding PBK1.

A method of treating type 1 diabetes in a subject is provided which includes delivering a mammalian pancreas-derived cell including a recombinant nucleic acid encoding PBK1 to a subject. In preferred embodiments, the cell is a glucose-sensing cell competent to secrete insulin. In particular embodiments, the mammalian pancreas-derived cell including a recombinant nucleic acid encoding PBK1 is delivered to the pancreas. In further embodiments, the microencapsulated mammalian pancreas-derived cell including a recombinant nucleic acid encoding PBK1 is delivered to liver or the kidney capsule of the subject.

An in vivo animal model for transplantation of exogenous cells expressing a transgene to the pancreas is exemplified by a model of type 1 diabetes generated by treatment of an animal with streptozotocin (STZ). Streptozotocin is well-known as a naturally occurring chemical that is particularly toxic to the insulin-producing beta cells of the pancreas. The STZ-diabetic animals will be transplanted with pancreatic beta cell line stably overexpressing PBK1 gene to test efficacy of the transplantation in the treatment of type 1 diabetes. Animals which may be used in a streptozotocin model of type 1 diabetes include, but are not limited to, rodents, rabbits and dogs.

In further embodiments, a nucleic acid encoding PBK1 is delivered to a subject to stimulate pancreatic beta cell differentiation and/or regeneration. Pancreatic β-cell differentiation/regeneration is measured by cell number counting and by immunofluorescence analysis of BrdU incorporation in pancreatic β-cell lines overexpressing the PBK-1 kinase.

Methods of identifying a PBK1 modulator are provided according to embodiments of the present invention which include contacting PBK1 with a putative modulator compound and assaying for a change in PBK1 activity. For example, a detected increase in PBK1 activity is indicative that the putative activator compound is an PBK1 activator. A detected decrease in PBK1 activity is indicative that the putative inhibitor compound is a PBK1 inhibitor. It is understood by the ordinarily skilled artisan that the detected increase or decrease in any of the inventive methods described herein comprehends reference to appropriate controls for the purposes of the particular method.

An assay used in methods of identifying a PBK1 modulator or in methods of screening described herein may have any of various formats, including, but not limited to, cell-based and array assays. An array assay refers to an ordered array of one or more materials, such as an arrangement of addressable regions including putative activators, for example.

In particular embodiments, the inventive method includes detection of a change in secretagogue-stimulated insulin secretion, such as glucose-stimulated, GLP-1-stimulated and/or KCl-stimulated insulin secretion from a cell expressing PBK1. A cell expressing PBK1 is a mammalian pancreas-derived cell in particular embodiments of an inventive method. For example, a cell expressing PBK1 for use in an assay for detecting modulated PBK1 activity following contact with a putative modulator is a MIN6 cell containing a recombinant nucleic acid encoding PBK1.

Assays for modulator activity or for the screening described herein are optionally performed using a transgenic non-human animal, such as a transgenic mouse, having targeted deletion or overexpression of the PBK-1 gene, for example to test efficacy and specificity of PBK-1 modulator compounds. Methods for targeted deletion or overexpression of a gene in a cell and/or in an animal, such as a transgenic mouse, are known in the art as exemplified by description in references including, but not limited to, U.S. Pat. Nos. 5,994,618 and 6,891,082, Nagy, A. et al., Manipulating the Mouse Embryo: A Laboratory Manual, $3^{rd}$ ed., Cold Spring Harbor Laboratory, Cold Spring Harbor, N.Y., 2002 and Pinkert, C. A., Transgenic Animal Technology, A Laboratory Handbook, $2^{nd}$ ed., Academic Press, 2002. See also Kishi M. et al. (2005) Science 37: 929-931.

A pharmaceutical composition for treatment of type 2 diabetes in a subject is provided which includes a modulator of PBK1. A PBK1 modulator is an activator or inhibitor of PBK-1 activity in particular embodiments.

In particular embodiments, a PBK1 modulator or agent described herein is formulated for oral delivery to a subject, in particular a subject having need of treatment for type 2 diabetes. In further embodiments, the pharmaceutical composition is formulated for parenteral, nasal, topical, ocular, buccal, pulmonary, or rectal delivery to the subject.

Formulation of pharmaceutical compositions for particular routes of administration is known in the art and is described in detail in references such as Allen, L. V. et al., Ansel's Pharmaceutical Dosage Forms and Drug Delivery Systems, $8^{th}$ ed., Lippincott, Williams & Wilkins, 2005; and Remington: The Science and Practice of Pharmacy, $21^{st}$ ed., Lippincott, Williams & Wilkins, 2006.

The terms "subject" and "patient" are used interchangeably herein and refer to individual animals, particularly mammals, including, but not limited to, humans.

The invention comprehends PBK1 as a drug target to screen compounds to be used for the treatment of type 2 diabetes. In particular embodiments, activators of AMPK (5'-AMP-activated protein kinase), related compounds and derivatives are PBK1 activators for the treatment of type 2 diabetes which improve glucose-sensing of the pancreatic beta-cells.

In further embodiments, inhibitors of PBK-1 are identified. PBK-1 inhibitors are useful, for instance, to prevent/treat hyperglycemia-induced apoptosis of pancreatic beta cells, or used as reference compounds in the methods described herein.

Embodiments of inventive compositions and methods are illustrated in the following examples. These examples are provided for illustrative purposes and are not considered limitations on the scope of inventive compositions and methods.

EXAMPLES

Example 1

Cloning and Expression

Molecular Cloning of PBK1

The coding region of the human PBK1 cDNA (SEQ ID NO: 18; NCBI Acc. AF533876) is amplified by PCR from human fetal brain marathon-ready cDNA(BD Bioscience) using primers by 5'-CGATGACATCGACGGGGAAGGAC-3' (SEQ ID NO: 7) and 5'-GATGGCCTCGTGGAGGTGA-CATG-3' (SEQ ID NO: 8) and subcloned into Srf-1 site of pCR-Script-Amp SK(+) vector. A flag-tagged version of PBK1 is generated by PCR amplification by using primer pairs 5'-GCCACCATGGATTACAAGGATGACGAC-GATAAGACATCGACGGGGAAGGACGGCG GC-3' (SEQ ID NO: 9), and 5'-GATGGCCTCGTGGAGGTGA-CATG-3' (SEQ ID NO: 10). The resulting PCR product is cloned into Srf-1 sites of pCR-Script-Amp SK(+) vector, sequenced, and subcloned to the HindIII-Not1 sites of pcDNA3.1.

Retrovirus Expression Vector

The insert is excised with BamH1-Xho1 from pcDNA3.1-PBK1 and ligated into the BamH1 and Sal1 sites of pBabe-puro to generate pBabe-PBK1 for retroviral expression in MIN6 cells.

Mutants

Site-directed mutagenesis is performed by using Quick-change multi-site kit (Strategene). Amino acid residue Arg-48(K48M) or Thr-260(T260A) of PBK1 was replaced by Met and Ala, respectively. The primers for these two mutants are 5'-CCAGAAGGTGGCCATCATGATCGTCAAC-CGTGAG-3' (SEQ ID NO: 11) (K48M) and 5'-CGCCG-CACGCCGCCTCGCGCTAGAGCACATTCAG-3' (SEQ ID NO: 12) (T260A). The mutants are confirmed by sequencing analysis.

Cell Culture and Retroviral Infection

Pancreatic beta-cell line, Min6 cells, described in Miyazaki et al., Endocrinology, 1990 July; 127(1):126-32, are cultured in DMEM with 15% FBS, 25 mM glucose, 100 micromolar beta-mercaptoethanol, 100 units/ml penicillin/streptomycin. For retroviral infection, pBabe-puro constructs are used to transfect 293T-derived phoenix cells by the calcium phosphate method. Two days after transfection, supernatants containing viral particles are harvested and used to infect MIN6 cells. The cells are then selected by 1 microgram/ml puromycin.

Example 2

Human Tissue Distribution of PBK1 mRNA

Tissue distribution of PBK1 (pancreas brain kinase-1), also known as BRSK2, SAD-A, SAD1, STK29, PEN11B, C11orf7 (18, 19) is examined. Northern blot analysis shows that PBK1 is almost exclusively expressed in human pancreas and brain, and most abundantly in human pancreas (FIG. 1); implicating an important role for PBK1 in regulating pancreas function. Similar results were obtained when heart tissue was included in Northern blots. Northern blot analysis was carried out using multi-tissue blot from Clontech and radio-labeled human PBK1 as a probe.

Example 3

PBK1 Protein is Predominantly Expressed in Endocrine Islets

Figure 2:
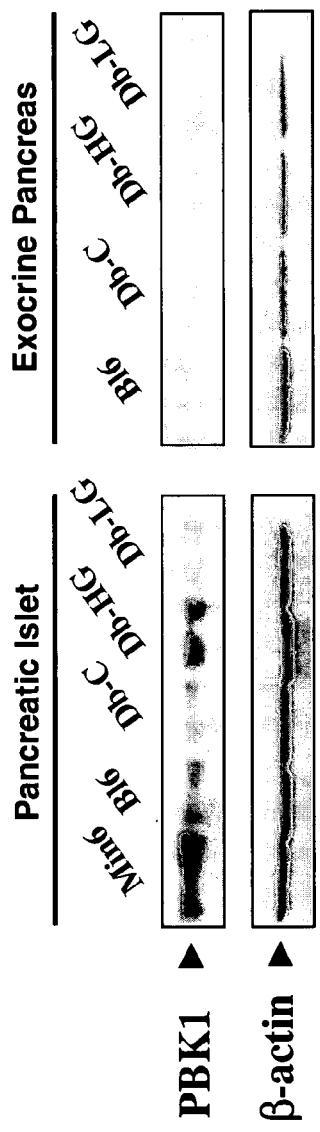
FIG. 2 depicts a western blot that indicates that PBK1 is predominantly expressed in endocrine islets, and that PBK1 protein expression was significantly up-regulated in islets of diabetic db mice.

PBK1 protein expression were analyzed by western blot analysis using mouse monoclonal antibody to PBK1 and protein lysate from Min6 cells, pancreatic islets and exocrine pancreas isolated from C57B16 (B16), non-diabetic control db mouse (Db-C), hyperglycemic db mouse (Db-HG), or db mouse under normalglycemia (Db-LG), respectively. The same blot was also used to analyze the expression level of β-actin as an internal control for sample loading. The results showed that PBK1 is predominantly expressed in endocrine islet, but not detectable in exocrine pancreas. The results also showed that PBK1 protein expression was significantly up-regulated in islets of diabetic db mice. See FIG. 2.

Example 4

PBK1 Overexpression Improved Glucose-Sensing by Min-6 Cells

Figure 3:
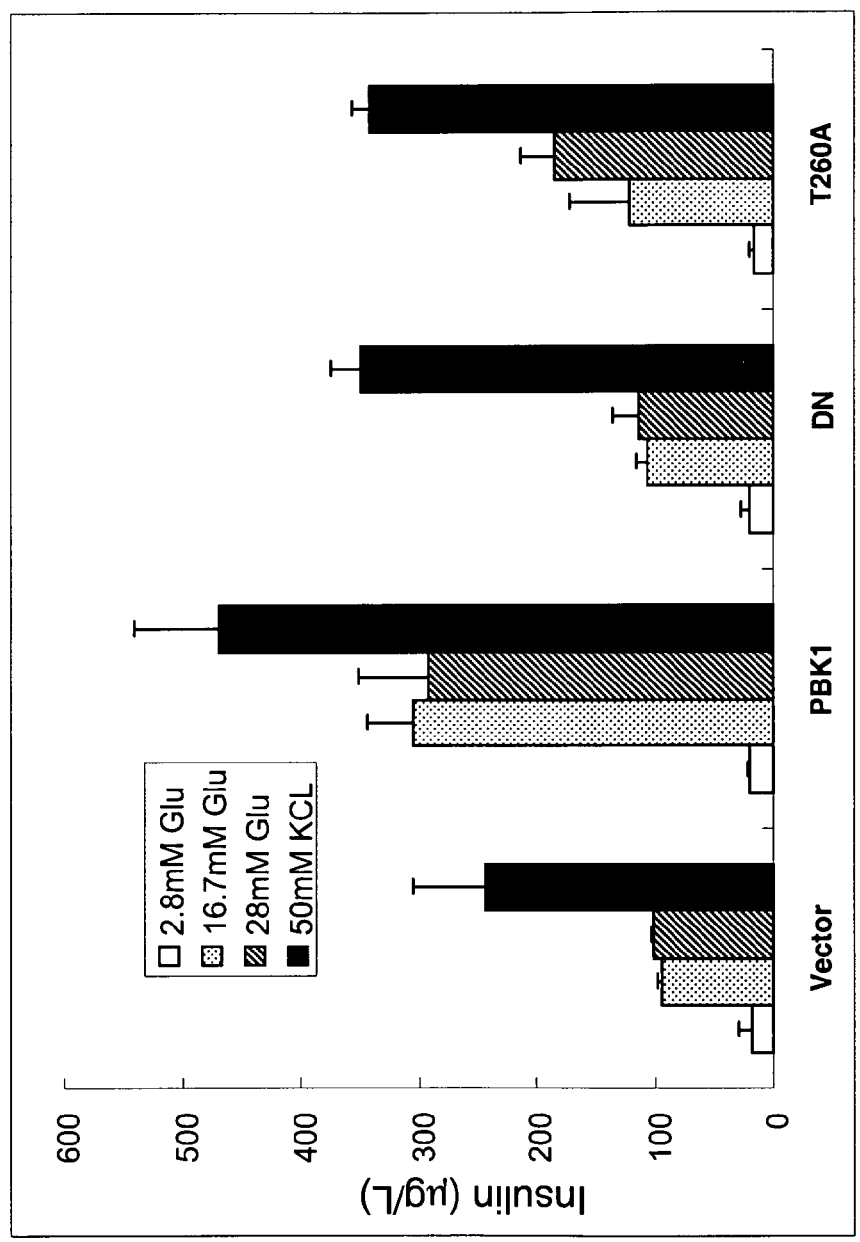
FIG. 3 graphically represents insulin levels at indicated glucose concentrations for Min-6 cells comprising vector, PBK1, a dominant negative mutant of PBK1 (DN), and a PKA phosphorylation defective mutant of PBK1 (T260A); demonstrating that PBK1 overexpression improved glucose-sensing by Min-6 cells.

Min-6 is a stable cell line derived from mouse pancreatic beta cells (25). In comparison with other pancreatic beta-cell lines, MIN6 cells maintain the integrity of glucose-sensing ability. To achieve high transfection rates for the expression of PBK1 in MIN6 cells, a recombinant retroviral expression system was created for PBK1 as described above, and a flag tagged expression vector for PBK1 is generated to facilitate analysis of its expression in MIN6 cells, a mouse islet beta-cell line. As shown in FIG. 3, overexpression of PBK1 in MIN6 cells significantly enhances glucose and KCl stimulated insulin secretion. The effect of PBK1 on insulin secretion is fully dependent on its kinase activity.

The Min-6 cells were cultured in DMEM medium containing 4.5 g/l glucose and L-glutamine, and were infected with recombinant retroviruses overexpressing the human PBK1, a dominant negative mutant of PBK1 (DN), or a PKA phosphorylation defective mutant of PBK1 (T260A). The dominant negative mutant was generated by replacing lysine at aa 48 with methionine. The PKA defective mutant was generated by replacing threonine at aa 260 with an alanine. The infected Min-6 cells were selected for puromycin resistance as a stable pool. For measurement of glucose sensing by Min-6 cells, the stable pool of the infected Min-6 cells were preincubated for 1 hour at 37° C. in Krebs Ringer buffer containing 0 mM glucose, followed by 2 hour incubation with the indicated concentration of 2.8 mM, 16.7 mM, and 28 mM of glucose or 50 mM KCl. The supernatants were then collected and analyzed for insulin levels by radioimmuno assays using a kit from Linco Research, Inc. With respect to DN, mutation of the key amino acids for the kinase activation of PBK completely abolished its effect on insulin secretion. With respect to T260A, the mutant PBK1 partially lost its ability to improve insulin secretion by glucose and KCl (FIG. 3). The results showed that the wild type PBK1, but not the mutants, potentiated glucose- and KCl-stimulated insulin secretion.

Example 5

PBK1 Deficiency Impaired Glucose-Stimulated Insulin Secretion from Min-6 Cells

Figure 4:
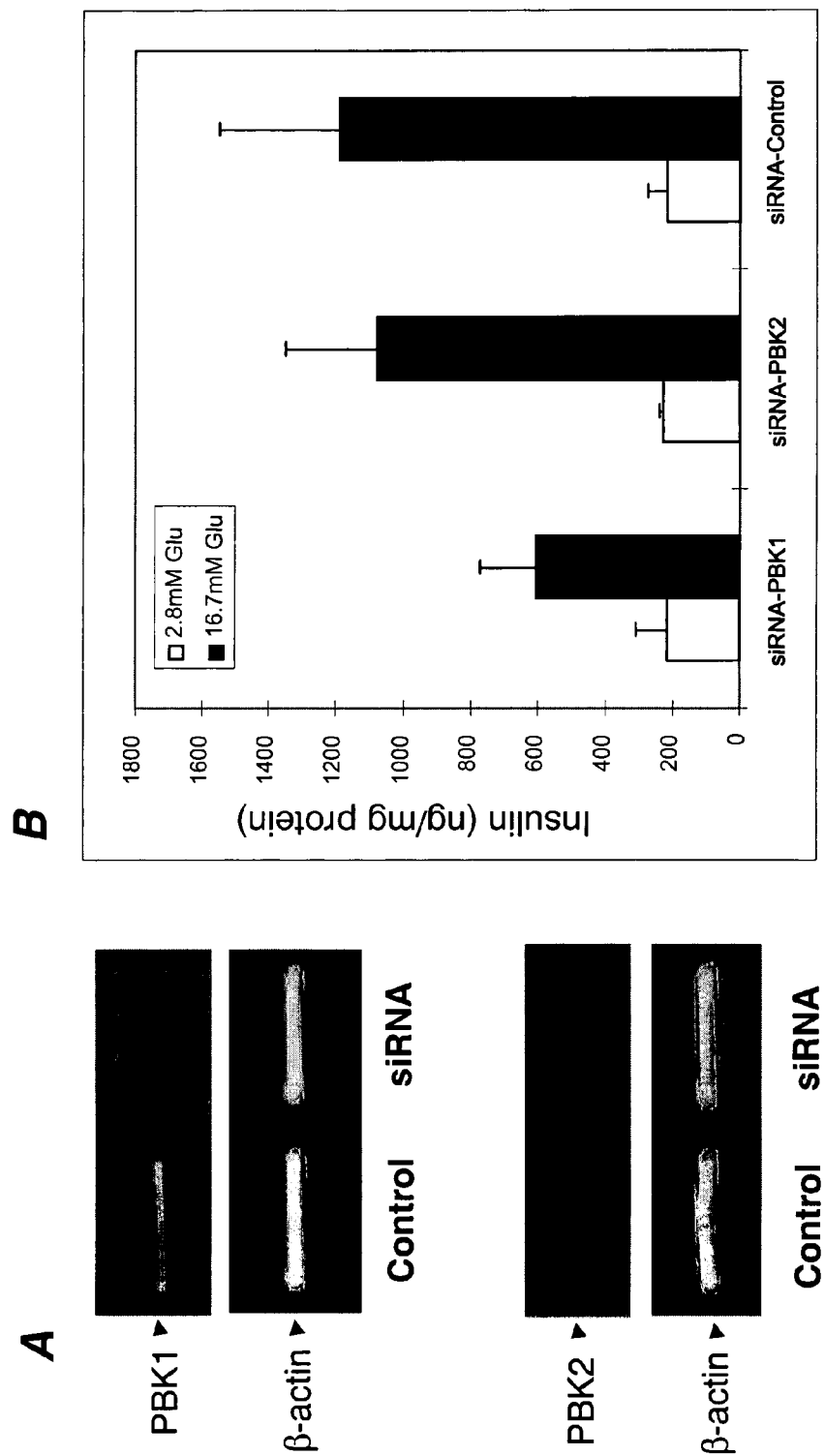
FIGS. 4A and 4B depict RT-PCR and insulin secretion data related to inhibition of PBK1 and PBK2 mRNA expression.

Endogenous mouse PBK1 (also known as SAD-A; BRSK2) and PBK2 (also known as SAD-B; BRSK1) mRNA expression was inhibited by transient transfection of Min-6 cells with 200 nM of siRNAs targeting the coding region of the mouse PBK1 (194-214: 5'-AGCGAGAGATTGC-CATCTTGA-3') (SEQ ID NO: 16) and PBK2 (468-488: 5-GCCAGAGAACCTGCTGTTGGA-3') (SEQ ID NO: 17) coding regions or a scrambled-sequence siRNA as a negative control (Dharmacon) using Lipofectamine 2000 (Invitrogen). Efficiency of PBK1 and PBK2 knockdown were assessed by RT-PCR. The results showed more than 70% reduction of the endogenous PBK1 and PBK2 mRNA expression (A). Sixty hours after the transfection, insulin secretion was analyzed from the Min-6 cells as described in FIG. 4. The results showed that deficiency of PBK1, but not PBK2, resulted in impaired glucose sensing by Min-6 cells (B).

Example 6

PBK1 Deficiency in Mice Caused Diabetes

Figure 5:
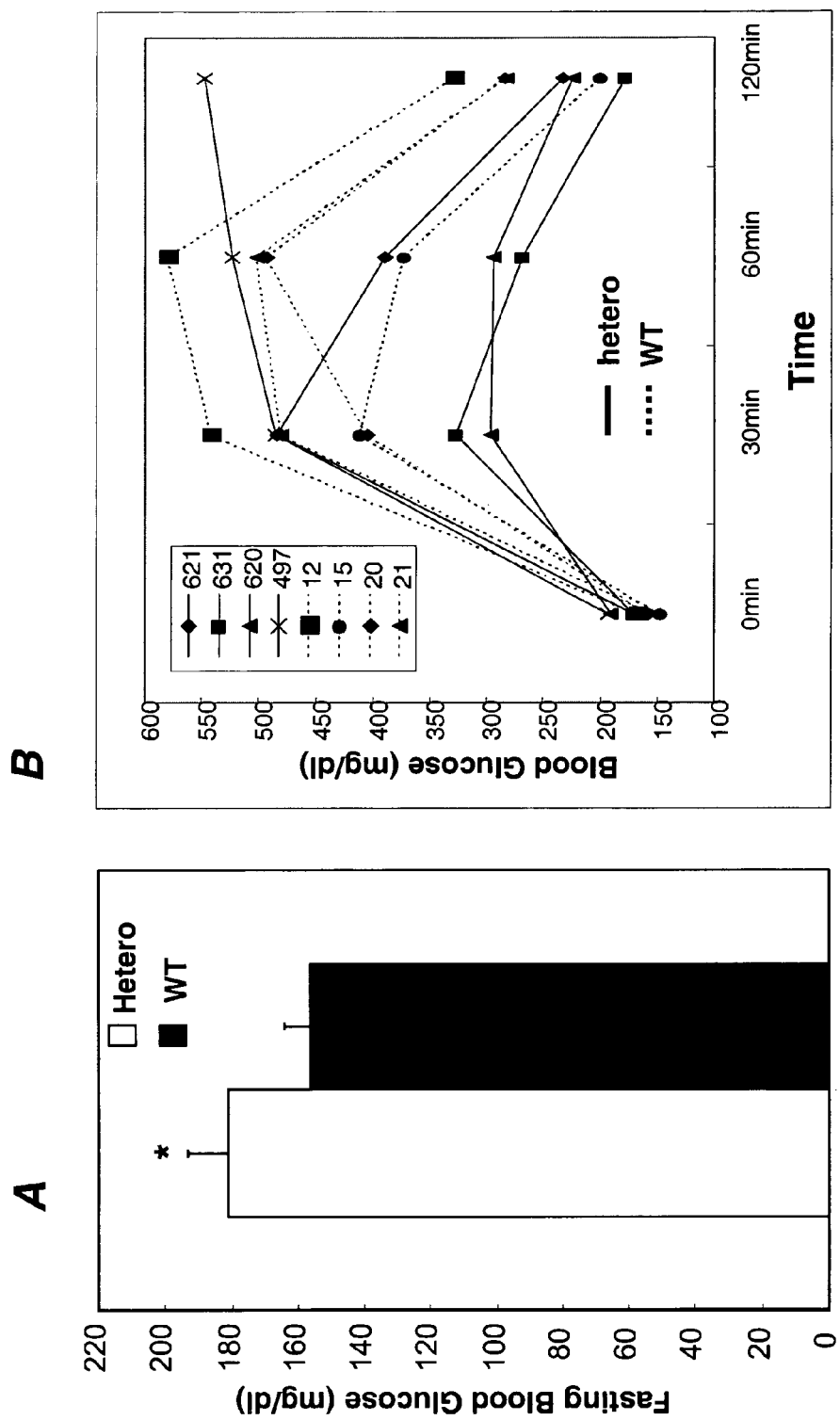
FIGS. 5A and 5B graphically represent a time course for oral glucose tolerance in PBK1 heterozygous knockout mice and wild type controls.

Oral glucose tolerance test were carried out in awakening PBK1 heterozygous knockout mice and the wild type controls to analyze the onset of diabetes. The heterozygous PBK1 knockout (n=4) and the wild type control mice (n=4) at three months of age on regular chow were fasted overnight and then analyzed for blood glucose levels using blood samples collected by tail bleeding (0 min). The mice were then given 50% glucose solution by oral gavage at 2.5 g glucose/kg body weight. Blood samples were collected from tail-bleeding at 30, 60, and 120 minutes, respectively, after the glucose overload and analyzed for glucose levels by glucose meter. The results (FIG. 5) showed that the heterozygous PBK1 knockout mice have higher fasting blood glucose level (panel A). One of the heterozygous mice developed diabetes as judged by the fasting blood glucose level and glucose tolerance test (panel B).

Example 7

Subcellular Fractionation of PBK1

Figure 6:
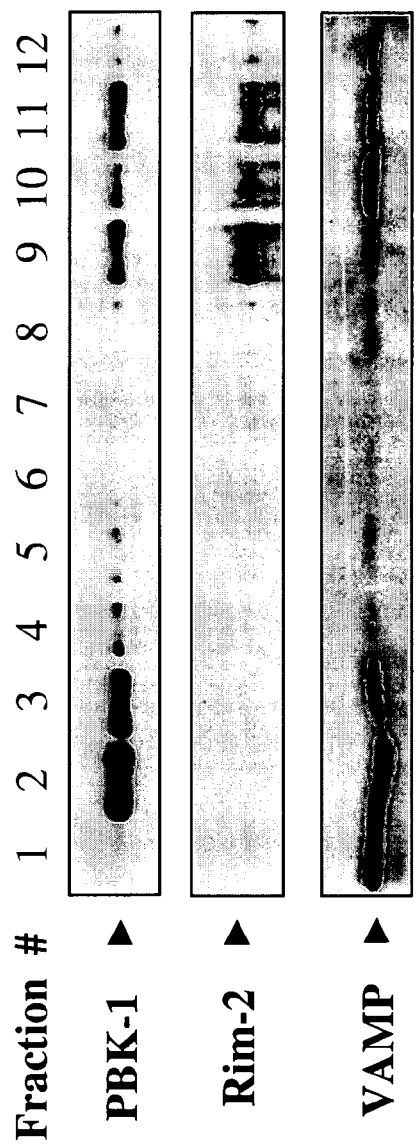
FIG. 6 depicts western blot data related to subcellular localization of recombinant PBK1.

PBK1 is associated with both synaptic-like microvesicles and insulin secretion granules. Subcellular localization of the recombinant PBK1 in MIN-6 cells was analyzed by sucrose gradient and Western blot analysis using markers for synaptic-like microvesicles and insulin secretion granules. As shown by FIG. 6, the recombinant PBK1 is co-localized with both Rim2 and VAMP2 in subcellular fractions segregated by sucrose gradient. Rim2 is a putative effector protein for Rab3s, synaptic GTP-binding proteins. RIM2 is localized close to the active zone at the synapse and regulates neurotransmitter releases (20). In insulin-secreting β-cells, Rim2 interacts with cAMP-binding protein cAMP-GEFII (or Epac 2), and mediates cAMP-dependent, PKA-independent insulin secretion (21). VAMP2 is associated with insulin secretory granules and regulates insulin exocytosis from pancreatic β-cells (22). The data support a dynamic role of PBK1 in regulating insulin secretion by interacting with proteins of different networks involved in insulin secretion.

Sucrose gradient fractionation is performed by the method of Mizuta et all (17). Briefly, a stable MIN6 cell clone overexpressing PBK1 is harvested by homogenization buffer containing 200 mM sucrose, 50 mM NaCl, 2 mM EGTA, 10 mM HEPES at pH7.2, and 1 mM phenylmethylsulfony fluoride and homogenized. The homogenate is centrifuged at 1770 g for 6 min at 4° C. The resulting postnuclear supernatant is applied to the top of sucrose gradients (0.4, 0.6, 0.8, 1.0, 1.4, 1.8 M) in 10 mM HEPES, pH 7.2, and 2 mM EGTA, and centrifuged at 55,000 g for 2 hours at 4° C. The fractions are collected from the top to bottom, precipitated with 15% trichloroacetic acid, and subjected to immunoblot analysis using anti-Flag antibody(Sigma), anti-Rim2 antibody (Synaptic Systems), and anti-VAMP2 antibody (Calbiochem).

Example 8

Polymorphism Analysis for Early Diagnosis of Type 1 Diabetes and Type 2 Diabetes PBK1 is localized on chromosome 11p15.5, an IDDM2 diabetic locus. Sequence analysis of the 3'-untranslated region revealed a polymorphism, described in Miura et al. (18), which can be used to predict the onset of type 2 diabetes. The polymorphism will be investigated by analyzing the patterns of DNA fragments from HhaI/BstUI digestion of genomic DNAs of the 3' untranslated region of PBK1 gene from diabetic and non-diabetic subjects. The genomic DNAs from diabetic and non-diabetic subjects will be amplified by PCR reactions (35 cycles of 94° C. for 30 seconds, 59° C. for 30 seconds, and 72° C. for 90 seconds) using a primer pair: 5'-GTCACCTGACCCCTCAGCAA-3' (SEQ ID NO: 13) and 5'-CACCAGCTCTGTCCTCAGAG-3' (SEQ ID NO: 14). The PCR product will be purified by Qiaquick PCR purification kit (Qiagen), digested with HhaI/BstUI, and separated on a 6% polyacrylamide gel.

Example 9

Early Diagnosis of Type 1 Diabetes

Type 1 diabetes is caused by autoimmune destruction of pancreatic beta cells, which generally occurs over a period of several years leading to the eventual onset of overt diabetes mellitus. During this extended pre-clinical phase, the characteristic circulation of autoantibodies against a variety of islet cell antigens including glutamic acid decarboxylase (GAD65), IA-2 (a tyrosine phosphatase-like protein), and insulin provides early markers of autoimmune disease activity as well as early diagnosis of type 1 diabetes. The present invention comprehends PBK1 as an autoantigen in type 1 diabetes, and that the autoantigen can be used as a marker for early diagnosis of type 1 diabetes by using enzyme-linked immunosorbent assay (ELISA), radioimmuno assays (RIA), and the like. In the ELISA assay, purified PBK1 protein will be used to detect the presence of antoantibodies to PBK1 from serum of type 1 diabetic patients. Methods for detecting presence or absence of autoantigens are known to the ordinarily skilled artisan. For example, such methods have been applied to detect presence or absence of GAD65 and other autoantigens (23).

Example 10

Application to Type 2 Diabetes

PBK1 can be used as a drug target to screen activator compounds for the treatment of diabetes, obesity, diabetic retinopathy, and other metabolic diseases. The screening process illustratively comprehends binding assay, kinase assay, and functional assay. PBK1 activators can be identified by measuring the binding potency of the compounds to the kinase ATP binding site through competition with a conjugated binding probe as described in reference 24. PBK1 activators are expected to stimulate kinase activity in a kinase assay. In the PBK1 kinase assay, purified PBK1 from E. coli or sf-9 insect cells are incubated in a kinase buffer (Cell Signaling Technology, USA) in the presence of 0.5 mM LNR peptide (KKLNRTLSFAEPG) (SEQ ID NO: 15) in the presence of 10 µM ATP, and 1 µl [γ-$^{32}$P]-ATP (5 µCi). After incubation at 30° C. for 30 min, 15 µl aceticacidglacial is added to stop the reaction. The kinase activity is quantified by radioactivity incorporated into the LNR peptide using phosphocellulose P-81 filter squares. For high throughput kinase assay for PBK1 activators, purified PBK1 protein is incubated with sepharose beads coupled with LNR peptide in the kinase buffer in the presence of 0.2 mM of [γ-$^{32}$P]-ATP for 30 min, and then washed three times before scintillation counting of radioactivity. In the functional assay, PBK1 activators are expected to potentiate glucose stimulated insulin secretion from isolated islet beta cells or cultured pancreatic beta cell lines, such as Min-6 cells. In this assay, addition of a PBK1 activator potentiates glucose stimulated insulin secretion in a glucose-dependent manner, but is ineffective in the absence of glucose, as demonstrated by FIG. 3.

Example 11

Sequence Data

SEQ ID NO.'s: 1 and 2 are with reference to: Accession NO. NM_003957; 3506 bp; Homo sapiens BR serine/threonine kinase 2 (BRSK2) setting forth:

/translation =
"MTSTGKDGGAQHAQYVGPYRLEKTLGKGQTGLVKLGVHCVTCQK

VAIKIVNREKLSESVLMKVEREIAILKLIEHPHVLKLHDVYENKKYLYLVLEHVSGGE

LFDYLVKKGRLTPKEARKFFRQIISALDFCHSHSICHRDLKPENLLLDEKNNIRIADF

GMASLQVGDSLLETSCGSPHYACPEVIRGEKYDGRKADVWSCGVILFALLVGALPFDD

DNLRQLLEKVKRGVFHMPHFIPPDCQSLLRGMIEVDAARRLTLEHIQKHIWYIGGKNE

PEPEQPIPRKVQIRSLPSLEDIDPDVLDSMHSLGCFRDRNKLLQDLLSEEENQEKMIY

FLLLDRKERYPSQEDEDLPPRNEIDPPRKRVDSPMLNRHGKRRPERKSMEVLSVTDGG

SPVPARRAIEMAQHGQRSRSISGASSGLSTSPLSSPRVTPHPSPRGSPLPTPKGTPVH

TPKESPAGTPNPTPPSSPSVGGVPWRARLNSIKNSFLGSPRFHRRKLQVPTPEEMSNL

TPESSPELAKKSWFGNFISLEKEEQIFVVIKDKPLSSIKADIVHAFLSIPSLSHSVIS

QTSFRAEYKATGGPAVFQKPVKFQVDITYTEGGEAQKENGIYSVTFTLLSGPSRRFKR

VVETIQAQLLSTHDPPAAQHLSDTTNCMEMMTGRLSKCGIIPKS"

ORIGIN
       1 gctgttcggc tcagctgcac ggctcggctc ggctcggctc ggctcggctg cgcggccgct
      61 gacgggcgtg cgctggggc gcggggcgcg gggcgcgggc ctcggcggcg gcggcggcgg
     121 cggcggcgga agccaggtgc ccccgcccgc cctgtcctct cgacgaggcg gaggcgtcgc
     181 cgcgggccag gcctcggact gccgcgtcgg agtggacgcg ggggcggcg gcgcgggcgg
     241 acgcgggcgg cgcgaagcag cggggcccgc ggggcgccc cggccgggtc ggcgcggacg
     301 gcactcggcg gacgcgggcg gacgctgggc ggccccctccc tgcccgcgcg cccgggcgcc
     361 cctggccggc gccgggcccc agagcgatga catcgacggg aaggacggc ggcgcgcagC
     421 acgcgcagta tgttgggccc taccggctgg agaagacgct gggcaagggg cagacaggtc
     481 tggtgaagct gggggttcac tgcgtcacct gccagaaggt ggccatcaag atcgtcaacc
     541 gtgagaagct cagcgagtcg gtgctgatga aggtggagcg ggagatcgcg atcctgaagc
     601 tcattgagca cccccacgtc ctaaagctgc acgacgttta tgaaaacaaa aatatttgt
     661 acctggtgct agaacacgtg tcaggtggtg agctcttcga ctaccggtg aagaagggga
     721 ggctgacgcc taaggaggct cggaagttct ccggcagat catctctgcg ctggacttct
     781 gccacagcca ctccatatgc cacagggatc tgaaacctga aaacctcctg ctggacgaga
     841 agaacaacat ccgcatcgca gactttggca tggcgtccct gcaggttggc gacagcctgt
     901 tggagaccag ctgtgggtcc ccccactacg cctgccccga ggtgatccgg ggggagaagt
     961 atgacggccg gaaggcggac gtgtggagct gcggcgtcat cctgttcgcc ttgctggtgg
    1021 gggctctgcc cttcgacgat dacaacttgc gacagctgct ggagaaggtg aagcggggcg
    1081 tgttccacat gccgcacttt atcccgcccg actgccagag tctgctacgg ggcatgatcg
    1141 aggtggacgc cgcacgccgc ctcacgctag agcacattca gaaacacata tggtatatag
    1201 ggggcaagaa tgagcccgaa ccagagcagc ccattcctcg caaggtgcag atccgctcgc
    1261 tgcccagcct ggaggacatc gaccccgacg tgctggacag catgcactca ctgggctgct
    1321 tccgagaccg caacaagctg ctgcaggacc tgctgtccga ggaggagaac caggagaaga
    1381 tgatttactt cctcctcctg gaccggaaag aaaggtaccc gagccaggag gatgaggacc
    1441 tgccccccg gaacgagata gaccctcccc ggaagcgtgt ggactcccg atgctgaacc
    1501 ggcacggcaa gcggcggcca gaacgcaaat ccatggaggt gctcagcgtg acggacggcg
    1561 gctcccggt gcctgcgcgg cgggccattg agatggccca gcacggccag aggtctcggt
    1621 ccatcagcgg tgcctcctca ggcctttcca ccagcccact cagcagcccc cgggtgaccc

```
-continued
1681 ctcacccctc accaagggc agtccctcc caccccaa ggggacacct gtccacacgc 1741 caaaggagag cccggctggc acgcccaacc ccacgccccc gtccagcccc agcgtcggag 1801 gggtgccctg gagggcgcgg ctcaactcca tcaagaacag ctttctgggc tcacccgct 1861 tccaccgccg gaaactgcaa gttccgacgc cggaggagat gtccaacctg acaccagagt 1921 cgtccccaga gctggcgaag aagtcctggt ttgggaactt catcagcctg gagaaggagg 1981 agcagatctt cgtggtcatc aaagacaaac ctctgagctc catcaaggct gacatcgtgc 2041 acgccttcct gtcgattccc agtctcagcc acagcgtcat ctcccaaacg agcttccggg 2101 ccgagtacaa ggccacgggg gggccagccg tgttccagaa gccggtcaag ttccaggttg 2161 atatcaccta cacggagggt ggggaggcgc agaaggagaa cggcatctac tccgtcacct 2221 tcacccctgct ctcaggcccc agccgtcgct tcaagagggt ggtggagacc atccaggccc 2281 agctgctgag cacacacgac ccgcctgcgg cccagcactt gtcagacacc actaactgta 2341 tggaaatgat gacggggcgg cttccaaat gtggaattat cccgaaaagt taacatgtca 2401 cctccacgag gccatcctct gtgaccgaag gcagctgctg cggacccgcc ctccctccgc 2461 tcctgctgtt gctgccggc agtgaggccc agcccagcgc ccgtccacc ccgcggcagc 2521 tcctcgcctc agctccgcac ggcccgtggg aggaaggcca ggctcggggg agcctcctcc 2581 agcccggccg acccggactc ccggtcacct gaccccctag caagaacagc ctgcctggtg 2641 gccttctggg gccaggaccc ctggtgggca acgtagccac aggaacaggc cccgtccacc 2701 gcctccacgc cgcacctgga ggcctcctcg caggcccgtg ccccgcctcc ctggctgcgc 2761 cgcctccgtg tagtcttggc ctcctcaggc tgcctcccgt cctctcgtct cacccgcgcc 2821 tcccttgcct catctgggc ggctgtgggc tctggcgctc ctctctggct gaggtggaaa 2881 cagagacacc ctgcggcacc agagccttcc cagcaggcca ggccgctggg ctgggatcag 2941 tgttatttat ttgccgtttt aatttatgga ttctccgcac ctctgttcag ggaagggcgg 3001 cggccacatc ccctgccgtc tgcgtgtctc aggcagtggg ggggctgggg ccagggcgcc 3061 ctctgaggac agagctggtg gggcgcgggg gggctggcga gctactgtaa actttaaaga 3121 attcctgcaa gatatttta taaacttttt tttcttggtg gtttttggaa aagggtgtgg 3181 gggtgggggc gccgctgggg cagggccagg ttttgtgttt tagtcccttg ctcctgcttc 3241 tttctacaca cacatctaaa gacggtgcgg ctcgctctgt catgggttcc gtctctctgt 3301 ggagaagcag ctccacctct gggggggctc ggggcagagg ggcggtgtct cgtagcgggc 3361 ggcagcgcca gcgcccctct gtcaggctgg gcaatcttg gttttgtgtc caaaggtgaa 3421 ggggtaggag gagggccctc agctggccct ccccacacac aggacggcag gggcactgtg 3481 aggcttttct tattaaaatg aaaaaa
```

SEQ ID NO.'s: 3 and 4 are with reference to: Accession NO. NM_032430; 3109 bp; *Homo sapiens* BR serine/threonine kinase 1 (BRSK1) setting forth:

/translation =
"MSSGAKEGGGGSPAYNLPHPHPHPPQHAQYVGPYRLEKTLGKGQ

TGLVKLGVHCITGQKVAIKIVNREKLSESVLMKVEREIAILKLIEHPHVLKLHDVYEN

KKYLYLVLENVSGGELFDYLVKKGRLTPKEARKFFRQIVSALDFCHSYSICHRDLKPE

NLLLDEKNNIRIADFGMASLQVGDSLLETSCGSPHYACPEVIKGEKYDGRRADMWSCG

VILFALLVGALPFDDDNLRQLLEKVKRGVFHMPHFIPPDCQSLLRGMIEVEPEKRLSL

-continued

EQIQKHPWYLGGKHEPDPCLEPAPGRRVAMRSLPSNGELDPDVLESMASLGCFRDRER

LHRELRSEEENQEKMIYYLLLDRKERYPSCEDQDLPPRNDVDPPRKRVDSPMLSRHGK

RRPERKSMEVLSITDAGGGGSPVPTRRALEMAQHSQRSRSVSGASTGLSSSPLSSPRS

PVFSFSPEPGAGDEARGGGSPTSKTQTLPSRGPRGGGAGEQPPPPSARSTPLPGPPGS

PRSSGGTPLHSPLHTPRASPTGTPGTTPPPSPGGGVGGAAWRSRLNSIRNSFLGSPRF

HRRKMQVPTAEEMSSLTPESSPELAKRSWFGNFISLDKEEQIFLVLKDKPLSSIKADI

VHAFLSIPSLSHSVLSQTSFRAEYKASGGFSVFQKPVRFQVDISSSEGPEPSPRRDGS

GGGGIYSVTFTLISGPSRRFKRVVETIQAQLLSTHDQPSVQALADEKNGAQTRPAGAP

PRSLQPPPGRPDPELSSSPRRGPPKDKKLLATNGTPLP"

ORIGIN
```
   1 gggggccggc cagaaacggg ctggggaggg ggggccccgc agccccctg ggccatgctg
  61 actcccgggg cctgaccccc cgggccagc cccctccc ccagctccgc ggcccgccga
 121 ctgggggggg ccagcccagc ccctgggga ccccggaga ggtgggggc agccggggg
 181 gccgggacgg agcggtcgcc ggccccacc ggagagacgg ggcgacggcc gcagggggg
 241 cggccggggg accggtcggg ccgggaccaa gggcaccatg tcgtccgggg ccaaggaggg
 301 aggtggggc tctcccgcct accacctccc ccaccccac cccacccac cccagcacgc
 361 ccaatatgtg ggccctatc ggctggagaa gacgctgggc aaaggacaga cagggctggt
 421 taaactcggg gtccactgca tcacgggtca aaggtcgcc atcaagatcg tgaaccggga
 481 gaagctgtcg gagtcggtgc tgatgaaggt ggagcgggag atcgccatcc tgaagctcat
 541 cgaacaccca catgtcctca agctccacga cgtctacgag aacaagaaat atttgtacct
 601 ggttctggag cacgtctcgg ggggtgagct attcgactac ctggtaaaga aggggagact
 661 gacgcccaag gaggcccgaa agttcttccg ccagattgtg tctgcgctgg acttctgcca
 721 cagctactcc atctgccaca gagacctaaa gcccgagaac ctgcttttgg atgagaaaaa
 781 caacatccgc attgcagact cggcatggc gtccctgcag gtggggaca gcctcctgga
 841 gaccagctgc gggtccccc attatgcgtg tccagaggtg attaaggggg aaaaatatga
 901 tggccgccgg gcagacatgt ggagctgtgg agtcatcctc ttcgccctgc tcgtgggggc
 961 tctgcccttt gatgacgaca acctccgcca gctgctggag aaggtgaaac ggggcgtctt
1021 ccacatgccc cacttcattc ctccagattg ccagagcctc ctgaggggaa tgatcgaagt
1081 ggagcccgaa aaaaggctca gtctggagca aattcagaaa catccttggt acctaggcgg
1141 gaaacacgag ccagacccgt gcctggagcc agccctggc cgccgggtag ccatgcggag
1201 cctgccatcc aacggagagc tggaccccga cgtcctagag agcatggcat cactgggctg
1261 cttcagggac cgcgagaggc tgcatcgcga gctgcgcagt gaggaggaga ccaagaaaa
1321 gatgatatat tatctgcttt tggatcggaa ggagcggtat cccagctgtg aggaccagga
1381 cctgcctccc cggaatgatg ttgaccccc ccggaagcgt gtggattctc ccatgctgag
1441 ccgtcacggg aagcggcgac cagagcggaa gtccatggaa gtcctgagca tcaccgatgc
1501 cgggggtggt ggctcccctg tacccacccg acgggccttg gagatggccc agcacagcca
1561 gagatcccgt agcgtcagtg gagcctccac gggtctgtcc tccagccctc taagcagccc
1621 aaggagtccg gtcttttcct tttcaccgga gccggggct ggagatgagg ctcgaggcgg
1681 gggctccccg acttccaaaa cgcagacgct gccttctcgg ggcccaggg gtggggcgc
1741 cggggagcag cccccgcccc ccagtgcccg ctccacaccc ctgccggcc cccaggctc
1801 cccgcgctcc tctggcggga cccccttgca ctcgcctctg cacacgcccc gggccagtcc
```

-continued

```
1861 caccgggacc ccggggacaa caccaccccc cagccccggc ggtggcgtcg ggggagccgc 1921 ctggaggagt cgtctcaact ccatccgcaa cagcttcctg ggctcccctc gctttcaccg 1981 gcgcaagatg caggtcccta ccgctgagga gatgtccagc ttgacgccag agtcctcccc 2041 ggagctggca aaacgctcct ggttcgggaa cttcatctcc ttggacaaag aagaacaaat 2101 attcctcgtg ctaaaggaca aacctctcag cagcatcaaa gcagacatcg tccatgcctt 2161 tctgtcgatc cccagcctga gtcacagtgt gctgtcacag accagcttca gggccgagta 2221 caaggccagt ggcggcccct ccgtcttcca aaagcccgtc cgcttccagg tggacatcag 2281 ctcctctgag gtccagagc cctcccgcg acgggacggc agcggaggtg gtggcatcta 2341 ctccgtcacc ttcactctca tctcgggtcc cagccgtcgg ttcaagcgag tggtggagac 2401 catccaggca cagctcctga gcactcatga ccagccctcc gtgcaggccc tgcagacga 2461 gaagaacggg gcccagaccc ggcctgctgg tgccccaccc cgaagcctgc agcccccacc 2521 cggccgccca gacccagagc tgagcagctc tccccgccga ggccccccca aggacaagaa 2581 gctcctggcc accaacggga cccctctgcc ctgacccccac ggggccgggg agggaggga 2641 ccccctcca cccccttcc gtgccccca actgtgaatc tgtaaataag gcccaaggaa 2701 catgtcggga gggggtgga cacaaaaacc ggccttgccc tgcagggatg gggctccaca 2761 ggccgtgccc aactgggggt ggttctaggg gaacaggggg cgggggagct gtttctattt 2821 tatttattga ttaatttatt attttattta ttgatcaatc tctctgcggg gtggggtggg 2881 ggagggacgg gagctggttg gggtggctta gcagatccgg acagggccct ctgtccctgt 2941 gtcgtcccca accccctctt cccgggcccc tcctcccctg gtcctccccc cacgaccttc 3001 tgtacggatt tgctctccgg aaggaattct ggtttcgcgt gatcctgcct gcgtccgtgt 3061 ctctgattcc gccggcggca aaaaaaaaaa aaaaaaaaa aaaaaaaa
```

SEQ ID NO's. 5 and 6 are with reference to:

```
NEDO human cDNA sequencing project; 3576 b.p.; Ninomiya,K. et al.
/organism = "Homo sapiens"
/mol_type = "mRNA"
/db_xref = "taxon:9606"
/clone = "BRAMY3018357"
/tissue_type = "amygdala"
/clone_lib = "BRAMY3"
/note = "cloning vector: pME18SFL3"
CDS 254 . . . 2554
/note = "unnamed protein product"
/codon_start = 1
/protein_id = "BAD18671.1"
/db_xref = "GI:47077575"

/translation =
"MSPEGHPSRWARPRRPCICPSSLCSPREPRSGPAVGRGGAAHHR

VPAGHTPGPQLLQPHLHLPQGQTWLCLQPSPAGLVKLGVHCVTCQKVAIKIVNREKLS

ESVLMKVEREIAILKLIEHPHVLKLHDVYENKKYLYLVLEHVSGGELFDYLVKKGRLT

PKEARKFFRQIISALDFCHSHSICHRDLKPENLLLDEKNNIRIADFGMASLQVGDSLL

ETSCGSPHYACPEVIRGEKYDGRKADVWSCGVILFALLVGALPFDDDNLRQLLEKVKR

GVFHMPHFIPPDCQSLLRGMIEVDAARRLTLEHIQKHIWYIGGKNEPEPEQPIPRKVQ

IRSLPSLEDIDPDVLDSMHSLGCFRDRNXLLQDLLSEEENQEKMIYFLLLDRKERYPS

QEDEDLPPRNEIDPPRKRVDSPMLNRHGKRRPERKSMEVLSVTDGGSPVPARRAIEMA

QHGQRSRSISGASSGLSTSPLSSPRVTPHPSRGSPLPTPKGTPVHTPKESPAGTPNP

TPPSSPSVGGVPWRARLNSIKNSFLGSPRFHRRKLQVPTPEEMSNLTPESSPELAKKS
```

-continued

WFGNFISLEKEEQIFVVIKDKPLSSIKADIVHAFLSIPSLSHSVISQTSFRAEYKATG

GPAVFQKPVKFQVDITYTEGGEAQKENGIYSVTFTLLSGPSRRFKRVVETIQAQLLST

HDPPAAQHLSDTTNCMEMMTGRLSKCDEKNGQAAQAPSTPAKRSAHGPLGDSAAAGPG

PGGDAEYPTGKDTAKMGPPTARREQP"

ORIGIN

```
   1 agtctcaggc tggctagttc ctccttcctg gtcactgagc cagccttgct gaggggagag
  61 cgggttctgg acgtgctctg agcttccttc ctcacagcct tgctcctggg ccagatcagc
 121 aggaaagcag ccagtgcccc gccatggcct gcccgggtgg ggtcctgaag ctggggccgg
 181 agcaggggc acagttctgc cccatctggc cctagtttgg ggagggagcc tgtagggca
 241 ccagcctcac cccatgagcc ctgagggcca ccccagccga tgggcacgtc cccgccggcc
 301 ctgcatctgt ccttcctccc tctgctcccc aagagagccc aggtctggcc cagcggtggg
 361 caggggaggg gccgcacatc acagagtgcc agctggccac actcccggcc cacagctgct
 421 ccagccgcac ctccaccttc ctcaaggcca gacctggctc tgcctgcagc ccagcccagc
 481 aggtctggtg aagctggggg ttcactgcgt cacctgccag aaggtggcca tcaagatcgt
 541 caaccgtgag aagctcagcg agtcggtgct gatgaaggtg gagcgggaga tcgcgatcct
 601 gaagctcatt gagcacccc acgtcctaaa gctgcacgac gtttatgaaa acaaaaaata
 661 tttgtacctg gtgctagaac acgtgtcagg tggtgagctc ttcgactacc tggtgaagaa
 721 ggggaggctg acgcctaagg aggctcggaa gttcttccgg cagatcatct ctgcgctgga
 781 cttctgccac agccactcca tatgccacag ggatctgaaa cctgaaaacc tcctgctgga
 841 cgagaagaac aacatccgca tcgcagactt tggcatggcg tccctgcagg ttggcgacag
 901 cctgttggag accagctgtg gtcccccca ctacgcctgc cccgaggtga tccgggggga
 961 gaagtatgac ggccggaagg cggacgtgtg gagctgcggc gtcatcctgt tcgccttgct
1021 ggtgggggct ctgcccttcg acgatgacaa cttgcgacag ctgctggaga aggtgaagcg
1081 gggcgtgttc cacatgccgc actttatccc gcccgactgc cagagtctgc tacgggcat
1141 gatcgaggtg gacgccgcac gccgcctcac gctagagcac attcagaaac acatatggta
1201 tatagggggc aagaatgagc ccgaaccaga gcagcccatt cctcgcaagg tgcagatccg
1261 ctcgctgccc agcctggagg acatcgaccc cgacgtgctg acagcatgc actcactggg
1321 ctgcttccga gaccgcaaca agctgctgca ggacctgctg tccgaggagg agaaccagga
1381 gaagatgatt tacttcctcc tcctggaccg gaaagaaagg taccgagcc aggaggatga
1441 ggacctgccc cccggaacg agatagacoc tccccggaag cgtgtggact ccccgatgct
1501 gaaccggcac ggcaagcggc ggccagaacg caaatccatg gaggtgctca gcgtgacgga
1561 cggcggctcc ccggtgcctg cgcggcgggc cattgagatg gcccagcacg gccagaggtc
1621 tcggtccatc agcggtgcct cctcaggcct ttccaccagc ccactcagca gcccccgggt
1681 gaccctcac ccctcaccaa ggggcagtcc cctccccacc cccaagggga cctgtcca
1741 cacgccaaag gagagcccgg ctggcacgcc caaccccacg ccccgtcca gccccagcgt
1801 cggagggtg ccctggaggg cgcggctcaa ctccatcaag aacagctttc tgggctcacc
1861 ccgcttccac cgccggaaac tgcaagttcc gacgccggag gagatgtcca acctgacacc
1921 agagtcgtcc ccagagctgg cgaagaagtc ctggtttggg aacttcatca gcctggagaa
1981 ggaggagcag atcttcgtgg tcatcaaaga caaacctctg agctccatca aggctgacat
2041 cgtgcacgcc ttcctgtcga ttcccagtct cagcccacagc gtcatctccc aaacgagctt
2101 ccgggccgag tacaaggcca cggggggcc agccgtgttc cagaagccgg tcaagttcca
```

```
2161 ggttgatatc acctacacgg agggtgggga ggcgcagaag gagaacggca tctactccgt 2221 caccttcacc ctgctctcag gccccagccg tcgcttcaag agggtggtgg agaccatcca 2281 ggcccagctg ctgagcacac acgacccgcc tgcggcccag cacttgtcag acaccactaa 2341 ctgtatggaa atgatgacgg ggcggctttc caaatgtgac gagaagaacg ggcaggcggc 2401 ccaggccccc agcacgcccg ccaagcggag tgcccacggc ccactcggtg actccgcggc 2461 cgctggccct ggccccggag gggacgccga gtacccaacg ggcaaggaca cggccaagat 2521 gggcccgccc accgcccgcc gcgagcagcc ttagacacac tagcccccccc ccccagcaca 2581 gcactgacag cggctgcctc gccgcccgcc gcccgccctg ccccgagtgg acccgcggcc 2641 gcgccgcccg tccgtccaga ctgttctcag agcctgggag gaaaggaaag gggcgttggg 2701 gccggcctgt gggctgcgcc acccgcgccc gctctctttt ctctctgtct ctgcctctgc 2761 ctgtctctga cagcatcgct tgtttccact ctgataccag gaattatccc gaaaagttaa 2821 catgtcacct ccacgaggcc atcctctgtg accgaaggca gctgctgcgg acccgccctc 2881 cctccgctcc tgctgttgct gccgggcagt gaggcccagc ccagcgcccc gtccaccccg 2941 cggcagctcc tcgcctcagc tccgcacggc ccgtgggagg aaggccaggc tcgggggagc 3001 ctcctccagc ccggccgacc cggactcccg gtcacctgac ccctcagcaa gaacagcctg 3061 cctggtggcc ttctggggcc aggaccctg gtgggcaacg tagccacagg aacaggcccc 3121 gtccaccgcc tccacgccgc acctggaggc ctcctcgcag gcccgtgccc cgcctccctg 3181 gccgcgccgc ctccgtgtag tcttggcctc ctcaggctgc ctcccgtcct ctcgtctcac 3241 ccgcgcctcc cttgcctcat ctggggcggc tgtgggctct ggcgctcctc tctggctgag 3301 gtggaaacag agacaccctg cggcaccaga gccttcccag caggccaggc cgctgggctg 3361 ggatcagtgt tatttatttg ccgtttttaat ttatggattc tccgcacctc tgttcaggga 3421 agggcggcgg ccacatcccc tgccgtctgc gtgtctcagg cagtgggggg gctggggcca 3481 gggcgccctc tgaggacaga gctggtgggg cgcgggggggg ctggcgagct actgtaaact 3541 ttaaagaatt cctgcaagat atttttataa actttt
```
                                                                    40

SEQ ID NO.'s: 18 and 19 are with reference to: Accession NO. AF533876; 3117 bp; *Homo sapiens* BR serine/threonine kinase 1 (BRSK2) setting forth:

/translation =
"MTSTGKDGGAQHAQYVGPYRLEKTLGKGQTGLVKLGVHCVTCQK

VAIKIVNREKLSESVLMKVEREIAILKLIEHPHVLKLHDVYENKKYLYLVLEHVSGGE

LFDYLVKKGRLTPKEARKFFRQIISALDFCHSHSICHRDLKPENLLLDEKNNIRIADF

GMASLQVGDSLLETSCGSPHYACPEVIRGEKYDGRKADVWSCGVILFALLVGALPFDD

DNLRQLLEKVKRGVFHMPHFIPPDCQSLLRGMSEVDAARRLTLEHIQKHIWYIGGKNE

PEPEQPIPRKVQIRSLPSLEDIDPDVLDSMHSLGCFRDRNKLLQDLLSEEENQEKMIY

FLLLDRKERYPSQEDEDLPPRNEIDPPRKRVDSPMLNRHGKRRPERKSMEVLSVTDGG

SPVPARRAIEMAQHGQRSRSISGASSGLSTSPLSSPRVTPHPSPRGSPLPTPKGTPVH

TPKESPAGTPNPTPPSSPSVGGVPWRARLNSIKNSFLGSPRFHRRKLQVPTPEEMSNL

TPESSPELAKKSWFGNFISLEKEEQIFVVIKDKPLSSIKADIVHAFLSIPSLSHSVIS

QTSFRAEYKATGGPAVFQKPVKFQVDITYTEGGEAQKENGIYSVTFTLLSCPSRRFKR

VVETIQAQLLSTHDPPAAQHLSDTTNCMEMMTGRLSKCGIIPKS"

ORIGIN

-continued

```
   1 tgttcggctc agctgcacgg ctcggctcgg ctcggctcgg ctcggctgcg cggccgctga
  61 cgggcgtgcg ctgggggcgc ggggcgcggg gcgcgggcct cggcggcggc ggcggcggcg
 121 gcggcggaag ccaggtgccc ccgcccgccc tgtcctctcg acgaggcgga ggcgtcgccg
 181 cgggccaggc ctcggactgc cgcgtcggag tggacgcggg gggcggcggc gcgggcggac
 241 gcgggcggcg cgaagcagcg gggcccgcgg gggcgccccg gccgggtcgg cgcggacggc
 301 actcggcgga cgcgggcgga cgctgggcgg ccccctccctg cccgcgcgcc cgggcgcccc
 361 tggccggcgc tgggccccag agcgatgaca tcgacgggga aggacggcgg cgcgcagcac
 421 gcgcagtatg ttgggcccta ccggctggag aagacgctgg gcaaggggca gacaggtctg
 481 gtgaagctgg gggttcactg cgtcacctgc cagaaggtgg ccatcaagat cgtcaaccgt
 541 gagaagctca gcgagtcggt gctgatgaag gtggagcggg agatcgcgat cctgaagctc
 601 attgagcacc cccacgtcct aaagctgcac gacgtttatg aaaacaaaaa atatttgtac
 661 ctggtgctag aacacgtgtc aggtggtgag ctcttcgact acctggtgaa gaaggggagg
 721 ctgacgccta aggaggctcg gaagttcttc cggcagatca tctctgcgct ggacttctgc
 781 cacagccact ccatatgcca cagggatctg aaacctgaaa acctcctgct ggacgagaag
 841 aacaacatcc gcatcgcaga ctttggcatg cgtccctgc aggttggcga cagcctgttg
 901 gagaccagct gtgggtcccc ccactacgcc tgccccgagg tgatccgggg ggagaagtat
 961 gacgccgga aggcggacgt gtggagctgc ggcgtcatcc tgttcgcctt gctggtgggg
1021 gctctgccct tcgacgatga caacttgcga cagctgctgg agaaggtgaa gcggggcgtg
1081 ttccacatgc cgcactttat cccgcccgac tgccagagtc tgctacgggg catgagcgag
1141 gtggacgccg cacgccgcct cacgctagag cacattcaga aacacatatg gtatatgggg
1201 ggcaagaatg agcccgaacc agagcagccc attcctcgca aggtgcagat ccgctcgctg
1261 cccagcctgg aggacatcga ccccgacgtg ctggacagca tgcactcact gggctgcttc
1321 cgagaccgca acaagctgct gcaggacctg ctgtccgagg aggagaacca ggagaagatg
1381 atttacttcc tcctcctgga ccggaaagaa aggtacccga gccaggagga tgaggacctg
1441 ccccccccgga acgagataga ccctccccgg aagcgtgtgg actccccgat gctgaaccgg
1501 cacggcaagc ggcggccaga acgcaaatcc atggaggtgc tcagcgtgac ggacggcggc
1561 tccccggtgc ctgcgcggcg ggccattgag atggcccagc acggcagag gtctcggtcc
1621 atcagcggtg cctcctcagg cctttccacc agcccactca gcagccccg ggtgacccct
1681 caccctcac caaggggcag tcccctcccc accccaagg ggacacctgt ccacacgcca
1741 aaggagagcc cggctggcac gcccaacccc acgcccccgt ccagcccccag cgtcggaggg
1801 gtgccctgga gggcgcggct caactccatc aagaacagct ttctgggctc accccgcttc
1861 caccgccgaa aactgcaagt tccgacgccg gaggagatgt ccaacctgac accagagtcg
1921 tccccagagc tggcgaagaa gtcctggttt gggaacttca tcagcctgga aaggaggag
1981 cagatcttcg tggtcatcaa agacaaacct ctgagctcca tcaaggctga catcgtgcac
2041 gccttcctgt cgattcccag tctcagccac agcgtcatct cccaaacgag cttccgggcc
2101 gagtacaagg ccacgggggg gccagccgtg ttccagaagc cggtcaagtt ccaggttgat
2161 atcacctaca cggagggtgg ggaggcgcag aaggagaacg gcatctactc cgtcaccttc
2221 accctgctct caggccccag ccgtcgcttc aagagggtgg tggagaccat ccaggcccag
2281 ctgctgagca cacacgaccc gcctgcggcc cagcacttgt cagacaccac taactgtatg
2341 gaaatgatga cggggcggct ttccaaatgt ggaattatcc cgaaaagtta acatgtcacc
2401 tccacgaggc catcctctgt gaccgaaggc agctgctgcg gacccgccct ccctccgctc
```

```
2461 ctgctgttgc tgccgggcag tgaggcccag cccagcgccc cgtccacccc gcggcagctc 2521 ctcgcctcag ctccgcacgg cccgtgggag gaaggccagg ctcgggggag cctcctccag 2581 cccggccgac ccggactccc ggtcacctga cccctcagca agaacagcct gcctggtggc 2641 cttctggggc caggaccccc ggtgggcaac gtagccacag gaacaggccc cgtccaccgc 2701 ctccacgccg cacctggagg cctcctgcag gcccgtgccc cgcctccctg gccgcgccgc 2761 ctccgtgtag tcttggcctc ctcaggctgc ctcccgtcct ctcgtctcac ccgcgcctcc 2821 cttgcctcat ctggggaggc tgtgggctct ggcgctcctc tctggctgag gtggaaacag 2881 agacaccctg cggcaccaga gccttcccag caggccaggc cgctgggctg ggatcagtgt 2941 tatttatttg ccgttttcca atttatggat tctccgcacc tctgttcagg gaagggcggc 3001 ggccacatcc cctgccgtct gcgtgtctca ggcagtgggg gggctggggc cagggcgccc 3061 tctgaggaca gagctggtgg ggcgcggggg ggctggcgag ctactgtaaa ctttaaa
```

REFERENCES

1. Zimmet, P., et al. (2001) Nature 414:782-787.
2. MacDonald, et al. (2005) Philosophical Transactions of the Royal Society of London—Series B: Biological Sciences 360:2211-2225.
3. Kasuga, M. (2006) Journal of Clinical Investigation 116: 1756-1760.
4. Prentki, M., et al. (2006) Journal of Clinical Investigation 116:1802-1812.
5. Poitout, V., et al. (2002) Endocrinology 143:339-342.
6. Weyer, C., et al. (1999) Journal of Clinical Investigation 104:787-794.
7. Leahy, J. L. (2005) Arch Med Res 36:197-209.
8. Butler, A. E., et al. (2003) Diabetes 52:102-110.
9. Rhodes, C. J. (2005) Science 307:380-384.
10. Efanova, I. B., et al. (1998) Journal of Biological Chemistry 273:33501-33507.
11. Maedler, K., et al. (2005) Journal of Clinical Endocrinology & Metabolism 90:501-506.
12. Baggio, L. L., et al. (2006) Annual Review of Medicine 57:265-281.
13. Mari, A., et al. (2006) Hormone & Metabolic Research 38:838-844.
14. Kendall, D. M., et al. (2005) Diabetes Care 28:1083-1091.
15. Kolterman, O. G., et al. (2005) American Journal of Health-System Pharmacy 62:173-181.
16. Drucker, D. J. (2006) Cell Metabolism 3:153-165.
17. Mizuta, M., et al. (1997) Diabetes 46:2002-2006.
18. Miura, K., et al. (1998) 11p15.5. Journal of Human Genetics 43:283-284.
19. Stanchi, F., et al. (2001) Yeast 18:69-80.
20. Wang, Y., et al. (2000) Journal of Biological Chemistry 275:20033-20044.
21. Kashima, Y., et al. (2001) Journal of Biological Chemistry 276:46046-46053.
22. Nevins, A. K., et al. (2005) Journal of Biological Chemistry 280:1944-1952.
23. Oak S. et al., (2008) Proc Natl Acad Sci USA, April 8; 105(14): 5471-6.
24. Vainshtein I. et al., (2002) J. Biomol Screen. December; 7(6):507-14.
25. Miyazaki J. et al, (1990) Endocrinology 127: 126-132.

Any patents or publications mentioned in this specification are incorporated herein by reference to the same extent as if each individual publication is specifically and individually indicated to be incorporated by reference. Amino acid and nucleic acid sequences for PBK1 are shown in appended pages marked "Appendix" which are considered part of this application and which are incorporated herein by reference in their entirety. Additionally U.S. Patent Application Publications 2003/0092036 and 2005/0125852 are incorporated herein by reference in their entirety.

The compositions and methods described herein are presently representative of preferred embodiments, exemplary, and not intended as limitations on the scope of the invention. Changes therein and other uses will occur to those skilled in the art. Such changes and other uses can be made without departing from the scope of the invention as set forth in the claims. All numerical ranges described herein include all integers and decimal values within the range and are also inclusive of the endpoints.

The invention claimed is:

1. A method of screening for a candidate agent or for an agent that treats a metabolic disease, said method comprising one or more of:
   a) contacting a PBK1 (pancreas brain kinase) protein with a test agent under conditions that promote binding of said test agent to said PBK1 protein, and detecting binding of said test agent to said PBK1 protein, wherein detecting binding of said test agent identifies a candidate agent for treating a metabolic disease; wherein said PBK1 comprises a protein at least 95% identical to PBK1 of SEQ ID NO:2, and wherein said disease is selected from type 2 diabetes, obesity, and diabetic retinopathy;
   b) contacting a PBK1 protein with a test agent or the candidate agent under conditions that promote kinase activity of said PBK1 protein, and detecting an increase in the kinase activity, wherein detecting an increase in the kinase activity identifies the test agent or the candidate agent as an agent that treats a metabolic disease; wherein said PBK1 comprises a protein at least 95% identical to PBK1 of SEQ ID NO:2, and wherein said disease is selected from type 2 diabetes, obesity, and diabetic retinopathy; and
   c) contacting a cell that expresses a PBK1 protein with a test agent or the candidate agent under conditions that promote glucose-stimulated insulin secretion from said cell, and detecting an increase in the glucose-stimulated insulin secretion from the cell compared to a control, wherein detecting an increase in the glucose-stimulated insulin secretion from the cell compared to a control identifies the test agent or the candidate agent as an agent that treats a metabolic disease; wherein said PBK1 comprises a protein at least 95% identical to PBK1 of SEQ ID NO:2, and wherein said disease is selected from type 2 diabetes, obesity, and diabetic retinopathy.

2. The method of claim 1, wherein said PBK1 protein is selected from a protein having a polypeptide sequence that has at least 96%, 97%, 98%, or 99% identity to the protein having a polypeptide sequence set forth in SEQ ID NO: 2.

3. The method of claim 2, wherein said PBK1 protein is selected from a protein having a polypeptide sequence set forth in SEQ ID NO: 2 or SEQ ID NO: 6.

4. The method of claim 1 comprising both a) and c), wherein a) is performed prior to c) and wherein the candidate agent of a) and the test agent of c) are identical.

5. The method of claim 1 comprising both b) and c), wherein b) is performed prior to c) and wherein the test agent of b) and the test agent of c) are identical.

6. The method of claim 1 comprising all of a), b) and c), wherein a) is performed prior to b), and b) is performed prior to c) and wherein the candidate agent of a), the test agent of b) and the test agent of c) are identical.

7. The method of claim 1 further comprising determining that the increase in the glucose-stimulated insulin secretion involves potentiation of secretagogue-stimulated insulin secretion from a cell that expresses a PBK1 protein.

8. The method of claim 1 wherein the cell is a mammalian pancreas-derived cell.

9. The method of claim 1 wherein the cell is a MIN6 cell.

10. The method of claim 1 wherein the cell contains a recombinant nucleic acid encoding a PBK1 protein.

11. A method of screening for a candidate agent or for an agent that treats a metabolic disease, said method comprising one or more of:
  a) contacting a PBK1 (pancreas brain kinase) protein comprising an amino acid sequence selected from the group consisting of: SEQ ID NO. 2, SEQ ID NO. 6, SEQ ID NO. 19 and a PBK1 protein encoded by a nucleic acid that hybridizes under high stringency conditions wherein the high stringency conditions include hybridization in a hybridization solution containing 7% SDS, 0.5 M NaPO$_4$, pH 7, 1 mM EDTA at 65° C. followed by one or more washes with a 0.1% SDS, 1×SSC solution at 65° C., to a nucleic acid selected from the group consisting of: SEQ ID NO. 1, SEQ ID NO. 3, SEQ ID NO.5 and SEQ ID NO. 18 with a test agent under conditions that promote binding of said test agent to said PBK1 protein, and detecting binding of said test agent to said PBK1 protein, wherein detecting binding of said test agent identifies a candidate agent for treating a metabolic disease; wherein said disease is selected from type 2 diabetes, obesity, and diabetic retinopathy;
  b) contacting a PBK1 protein comprising an amino acid sequence selected from the group consisting of: SEQ ID NO. 2, SEQ ID NO. 6, SEQ ID NO. 19 and a PBK1 protein encoded by a nucleic acid that hybridizes under high stringency conditions wherein the high stringency conditions include hybridization in a hybridization solution containing 7% SDS, 0.5 M NaPO$_4$, pH 7, 1 mM EDTA at 65° C. followed by one or more washes with a 0.1% SDS, 1×SSC solution at 65° C., to a nucleic acid selected from the group consisting of: SEQ ID NO. 1, SEQ ID NO. 3, SEQ ID NO.5 and SEQ ID NO. 18 with a test agent or the candidate agent under conditions that promote kinase activity of said PBK1 protein, and detecting an increase in the kinase activity, wherein detecting an increase in the kinase activity identifies the test agent or the candidate agent as an agent that treats a metabolic disease; wherein said disease is selected from type 2 diabetes, obesity, and diabetic retinopathy; and
  c) contacting a cell that expresses a PBK1 protein comprising an amino acid sequence selected from the group consisting of: SEQ ID NO. 2, SEQ ID NO. 6, and a PBK1 protein encoded by a nucleic acid that hybridizes under high stringency conditions wherein the high stringency conditions include hybridization in a hybridization solution containing 7% SDS, 0.5 M NaPO$_4$, pH 7, 1 mM EDTA at 65° C. followed by one or more washes with a 0.1% SDS, 1×SSC solution at 65° C., to a nucleic acid selected from the group consisting of: SEQ ID NO. 1, SEQ ID NO.5 and SEQ ID NO. 18 with a test agent or the candidate agent under conditions that promote glucose-stimulated insulin secretion from said cell, and detecting an increase in the glucose-stimulated insulin secretion from the cell compared to a control, wherein detecting an increase in the glucose-stimulated insulin secretion from the cell compared to a control identifies the test agent or the candidate agent as an agent that treats a metabolic disease; wherein said disease is selected from type 2 diabetes, obesity, and diabetic retinopathy.

* * * * *

SEQUENCE LISTING

```
<160> NUMBER OF SEQ ID NOS: 19

<210> SEQ ID NO 1
<211> LENGTH: 3506
<212> TYPE: DNA
<213> ORGANISM: Homo sapiens

<400> SEQUENCE: 1
gctgttcggc tcagctgcac ggctcggctc ggctcggctc ggctcggctg cgcggccgct      60
gacgggcgtg cgctgggggc gcggggcgcg gggcgcgggc ctcggcggcg gcggcggcgg     120
```

```
cggcggcgga agccaggtgc ccccgcccgc cctgtcctct cgacgaggcg gaggcgtcgc    180
cgcgggccag gcctcggact gccgcgtcgg agtggacgcg gggggcggcg gcgcgggcgg    240
acgcgggcgg cgcgaagcag cggggcccgc ggggggcgcc cggccgggtc ggcgcggacg    300
gcactcggcg gacgcgggcg gacgctgggc ggcccctccc tgcccgcgcg cccgggcgcc    360
cctggccggc gccgggcccc agagcgatga catcgacggg gaaggacggc ggcgcgcagc    420
acgcgcagta tgttgggccc taccggctgg agaagacgct gggcaagggg cagacaggtc    480
tggtgaagct gggggttcac tgcgtcacct gccagaaggt ggccatcaag atcgtcaacc    540
gtgagaagct cagcgagtcg gtgctgatga aggtggagcg ggagatcgcg atcctgaagc    600
tcattgagca cccccacgtc ctaaagctgc acgacgttta tgaaaacaaa aaatatttgt    660
acctggtgct agaacacgtg tcaggtggtg agctcttcga ctacctggtg aagaagggga    720
ggctgacgcc taaggaggct cggaagttct tccggcagat catctctgcg ctggacttct    780
gccacagcca ctccatatgc cacagggatc tgaaacctga aaacctcctg ctggacgaga    840
agaacaacat ccgcatcgca gactttggca tggcgtccct gcaggttggc gacagcctgt    900
tggagaccag ctgtgggtcc ccccactacg cctgccccga ggtgatccgg gggagaagt    960 atgacggccg gaaggcggac gtgtggagct gcggcgtcat cctgttcgcc ttgctggtgg   1020
gggctctgcc cttcgacgat gacaacttgc gacagctgct ggagaaggtg aagcggggcg   1080
tgttccacat gccgcacttt atcccgcccg actgccagag tctgctacgg ggcatgatcg   1140
aggtggacgc gcacgccgc ctcacgctag agcacattca gaaacacata tggtatatag   1200
ggggcaagaa tgagcccgaa ccagagcagc ccattcctcg caaggtgcag atccgctcgc   1260
tgcccagcct ggaggacatc gaccccgacg tgctggacag catgcactca ctgggctgct   1320
tccgagaccg caacaagctg ctgcaggacc tgctgtccga ggaggagaac caggagaaga   1380
tgatttactt cctcctcctg gaccggaaag aaaggtaccc gagccaggag gatgaggacc   1440
tgcccccccg gaacgagata gaccctcccc ggaagcgtgt ggactccccg atgctgaacc   1500
ggcacggcaa gcgcggccca gaacgcaaat ccatggaggt gctcagcgtg acggacggcg   1560
gctccccggt gcctgcgcgg cgggccattg agatggccca gcacggccag aggtctcggt   1620
ccatcagcgg tgcctcctca ggcctttcca ccagcccact cagcagcccc cgggtgaccc   1680 ctcaccccctc accaaggggc agtccctcc ccaccccaa ggggacacct gtccacacgc    1740
caaaggagag cccggctggc acgcccaacc ccacgccccc gtccagcccc agcgtcggag   1800
gggtgccctg gagggcgcgg ctcaactcca tcaagaacag ctttctgggc tcacccgct   1860 tccaccgccg gaaactgcaa gttccgacgc cggaggagat gtccaacctg acaccagagt   1920
cgtccccaga gctggcgaag aagtcctggt ttgggaactt catcagcctg gagaaggagg   1980
agcagatctt cgtggtcatc aaagacaaac ctctgagctc catcaaggct gacatcgtgc   2040
acgccttcct gtcgattccc agtctcagcc acagcgtcat ctcccaaacg agcttccggg   2100
ccgagtacaa ggccacgggg gggccagccc tgttccagaa gccggtcaag ttccaggttg   2160
atatcaccta cacggagggt ggggaggcgc agaaggagag cggcatctac tccgtcacct   2220
tcaccctgct ctcaggcccc agccgtcgct tcaagagggt ggtggagacc atccaggccc   2280
agctgctgag cacacacgac ccgcctgcgg cccagcactt gtcagacacc actaactgta   2340
tggaaatgat gacggggcgg ctttccaaat gtggaattat cccgaaaagt taacatgtca   2400 cctccacagag gccatcctct gtgaccgaag gcagctgctg cggacccgcc ctccctccgc   2460
tcctgctgtt gctgccgggc agtgaggccc agcccagcgc cccgtccacc ccgcggcagc   2520
```

-continued

```
tcctcgcctc agctccgcac ggcccgtggg aggaaggcca ggctcggggg agcctcctcc    2580
agcccggccg acccggactc ccggtcacct gacccctcag caagaacagc ctgcctggtg    2640
gccttctggg gccaggaccc ctggtgggca acgtagccac aggaacaggc cccgtccacc    2700
gcctccacgc cgcacctgga ggcctcctcg caggcccgtg ccccgcctcc ctggctgcgc    2760
cgcctccgtg tagtcttggc ctcctcaggc tgcctcccgt cctctcgtct cacccgcgcc    2820
tcccttgcct catctggggc ggctgtgggc tctggcgctc ctctctggct gaggtggaaa    2880
cagagacacc ctgcggcacc agagccttcc cagcaggcca ggccgctggg ctgggatcag    2940
tgttatttat ttgccgtttt aatttatgga ttctccgcac ctctgttcag ggaagggcgg    3000
cggccacatc ccctgccgtc tgcgtgtctc aggcagtggg ggggctgggg ccagggcgcc    3060
ctctgaggac agagctggtg gggcgcgggg gggctggcga gctactgtaa actttaaaga    3120
attcctgcaa gatattttta taaacttttt tttcttggtg gttttggaa aagggtgtgg     3180
gggtggggc gccgctgggg cagggccagg ttttgtgttt tagtcccttg ctcctgcttc     3240
tttctacaca cacatctaaa gacggtgcgg ctcgctctgt catgggttcc gtctctctgt    3300
ggagaagcag ctccacctct ggggggctc ggggcagagg ggcggtgtct cgtagcgggc     3360
ggcagcgcca gcgcccctct gtcaggctgg ggcaatcttg gttttgtgtc caaaggtgaa    3420
ggggtaggag gagggccctc agctggccct ccccacacac aggacggcag gggcactgtg    3480
aggcttttct tattaaaatg aaaaaa                                          3506
```

<210> SEQ ID NO 2
<211> LENGTH: 668
<212> TYPE: PRT
<213> ORGANISM: Homo sapiens

<400> SEQUENCE: 2

```
Met Thr Ser Thr Gly Lys Asp Gly Gly Ala Gln His Ala Gln Tyr Val
  1               5                  10                  15

Gly Pro Tyr Arg Leu Glu Lys Thr Leu Gly Lys Gly Gln Thr Gly Leu
                 20                  25                  30

Val Lys Leu Gly Val His Cys Val Thr Cys Gln Lys Val Ala Ile Lys
             35                  40                  45

Ile Val Asn Arg Glu Lys Leu Ser Glu Ser Val Leu Met Lys Val Glu
         50                  55                  60

Arg Glu Ile Ala Ile Leu Lys Leu Ile Glu His Pro His Val Leu Lys
 65                  70                  75                  80

Leu His Asp Val Tyr Glu Asn Lys Lys Tyr Leu Tyr Leu Val Leu Glu
                 85                  90                  95

His Val Ser Gly Gly Glu Leu Phe Asp Tyr Leu Val Lys Lys Gly Arg
            100                 105                 110

Leu Thr Pro Lys Glu Ala Arg Lys Phe Phe Arg Gln Ile Ile Ser Ala
            115                 120                 125

Leu Asp Phe Cys His Ser His Ser Ile Cys His Arg Asp Leu Lys Pro
        130                 135                 140

Glu Asn Leu Leu Leu Asp Glu Lys Asn Asn Ile Arg Ile Ala Asp Phe
145                 150                 155                 160

Gly Met Ala Ser Leu Gln Val Gly Asp Ser Leu Leu Glu Thr Ser Cys
                165                 170                 175

Gly Ser Pro His Tyr Ala Cys Pro Glu Val Ile Arg Gly Glu Lys Tyr
            180                 185                 190

Asp Gly Arg Lys Ala Asp Val Trp Ser Cys Gly Val Ile Leu Phe Ala
```

```
              195                 200                 205
Leu Leu Val Gly Ala Leu Pro Phe Asp Asp Asn Leu Arg Gln Leu
    210                 215                 220
Leu Glu Lys Val Lys Arg Gly Val Phe His Met Pro His Phe Ile Pro
225                 230                 235                 240
Pro Asp Cys Gln Ser Leu Leu Arg Gly Met Ile Glu Val Asp Ala Ala
                245                 250                 255
Arg Arg Leu Thr Leu Glu His Ile Gln Lys His Ile Trp Tyr Ile Gly
                260                 265                 270
Gly Lys Asn Glu Pro Glu Pro Glu Gln Pro Ile Pro Arg Lys Val Gln
            275                 280                 285
Ile Arg Ser Leu Pro Ser Leu Glu Asp Ile Asp Pro Asp Val Leu Asp
        290                 295                 300
Ser Met His Ser Leu Gly Cys Phe Arg Asp Arg Asn Lys Leu Leu Gln
305                 310                 315                 320
Asp Leu Leu Ser Glu Glu Glu Asn Gln Glu Lys Met Ile Tyr Phe Leu
                325                 330                 335
Leu Leu Asp Arg Lys Glu Arg Tyr Pro Ser Gln Glu Asp Glu Asp Leu
                340                 345                 350
Pro Pro Arg Asn Glu Ile Asp Pro Arg Lys Arg Val Asp Ser Pro
            355                 360                 365
Met Leu Asn Arg His Gly Lys Arg Pro Glu Arg Lys Ser Met Glu
    370                 375                 380
Val Leu Ser Val Thr Asp Gly Gly Ser Pro Val Pro Ala Arg Arg Ala
385                 390                 395                 400
Ile Glu Met Ala Gln His Gly Gln Arg Ser Arg Ser Ile Ser Gly Ala
                405                 410                 415
Ser Ser Gly Leu Ser Thr Ser Pro Leu Ser Ser Pro Arg Val Thr Pro
            420                 425                 430
His Pro Ser Pro Arg Gly Ser Pro Leu Pro Thr Pro Lys Gly Thr Pro
            435                 440                 445
Val His Thr Pro Lys Glu Ser Pro Ala Gly Thr Pro Asn Pro Thr Pro
    450                 455                 460
Pro Ser Ser Pro Ser Val Gly Gly Val Pro Trp Arg Ala Arg Leu Asn
465                 470                 475                 480
Ser Ile Lys Asn Ser Phe Leu Gly Ser Pro Arg Phe His Arg Arg Lys
                485                 490                 495
Leu Gln Val Pro Thr Pro Glu Glu Met Ser Asn Leu Thr Pro Glu Ser
            500                 505                 510
Ser Pro Glu Leu Ala Lys Lys Ser Trp Phe Gly Asn Phe Ile Ser Leu
        515                 520                 525
Glu Lys Glu Glu Gln Ile Phe Val Val Ile Lys Asp Lys Pro Leu Ser
    530                 535                 540
Ser Ile Lys Ala Asp Ile Val His Ala Phe Leu Ser Ile Pro Ser Leu
545                 550                 555                 560
Ser His Ser Val Ile Ser Gln Thr Ser Phe Arg Ala Glu Tyr Lys Ala
                565                 570                 575
Thr Gly Gly Pro Ala Val Phe Gln Lys Pro Val Lys Phe Gln Val Asp
                580                 585                 590
Ile Thr Tyr Thr Glu Gly Gly Glu Ala Gln Lys Glu Asn Gly Ile Tyr
                595                 600                 605
Ser Val Thr Phe Thr Leu Leu Ser Gly Pro Ser Arg Arg Phe Lys Arg
    610                 615                 620
```

```
Val Val Glu Thr Ile Gln Ala Gln Leu Leu Ser Thr His Asp Pro Pro
625                 630                 635                 640

Ala Ala Gln His Leu Ser Asp Thr Thr Asn Cys Met Glu Met Met Thr
                645                 650                 655

Gly Arg Leu Ser Lys Cys Gly Ile Ile Pro Lys Ser
            660                 665

<210> SEQ ID NO 3
<211> LENGTH: 3109
<212> TYPE: DNA
<213> ORGANISM: Homo sapiens

<400> SEQUENCE: 3
gggggccggc cagaaacggg ctggggaggg ggggccccgc agccccctg ggccatgctg         60 actcccgggg cctgaccccc ccgggccagc cccccctccc ccagctccgc ggcccgccga       120
ctgggggggg ccagcccagc cccctgggga ccccggaga ggtgggggc agccgggggg        180 gccgggacgg agcggtcgcc ggcccccacc ggagagacgg ggcgacggcc gcaggggggg       240
cggccggggg accggtcggg ccgggaccaa gggcaccatg tcgtccgggg ccaaggaggg       300
aggtgggggc tctcccgcct accacctccc ccaccccac ccccacccac ccagcacgc        360 ccaatatgtg ggcccctatc ggctggagaa gacgctgggc aaaggacaga cagggctggt       420
taaactcggg gtccactgca tcacgggtca gaaggtcgcc atcaagatcg tgaaccggga       480
gaagctgtcg gagtcggtgc tgatgaaggt ggagcgggag atcgccatcc tgaagctcat       540
cgaacaccca catgtcctca agctccacga cgtctacgag aacaagaaat atttgtacct       600
ggttctggag cacgtctcgg ggggtgagct attcgactac ctggtaaaga aggggagact       660
gacgcccaag gaggcccgaa agttcttccg ccagattgtg tctgcgctgg acttctgcca       720
cagctactcc atctgccaca gagacctaaa gcccgagaac ctgcttttgg atgagaaaaa       780
caacatccgc attgcagact cggcatggc gtccctgcag gtgggggaca gcctcctgga       840
gaccagctgc gggtccccc attatgcgtg tccagaggtg attaagggg aaaaatatga        900 tggccgccgg gcagacatgt ggagctgtgg agtcatcctc ttcgccctgc tcgtgggggc       960
tctgcccttt gatgacgaca acctccgcca gctgctggag aaggtgaaac ggggcgtctt      1020
ccacatgccc cacttcattc ctccagattg ccagagcctc ctgaggggaa tgatcgaagt      1080
ggagcccgaa aaaaggctca gtctggagca aattcagaaa catccttggt acctaggcgg      1140
gaaacacgag ccagacccgt gcctggagcc agccccctggc cgccgggtag ccatgcggag      1200
cctgccatcc aacggagagc tggaccccga cgtcctagag agcatggcat cactgggctg      1260
cttcagggac cgcgagaggc tgcatcgcga gctgcgcagt gaggaggaga accaagaaaa      1320
gatgatatat tatctgcttt tggatcggaa ggagcggtat cccagctgtg aggaccagga      1380
cctgcctccc cggaatgatg ttgaccccc ccggaagcgt gtggattctc ccatgctgag       1440
ccgtcacggg aagcggcgac cagagcggaa gtccatggaa gtcctgagca tcaccgatgc      1500 cggggggtggt ggctcccctg tacccacccg acgggccttg gagatggccc agcacagcca      1560
gagatcccgt agcgtcagtg agcctccac gggtctgtcc tccagccctc taagcagccc      1620
aaggagtccg gtctttcct tttcaccgga gccgggggct ggagatgagg ctcgaggcgg      1680
gggctccccg acttccaaaa cgcagacgct gccttctcgg ggcccagggg gtggggcgc       1740 cggggagcag ccccgcccc ccagtgcccg ctccacaccc ctgcccgcc cccaggctc         1800 cccgcgctcc tctggcggga ccccccttgca ctcgcctctg cacacgcccc gggccagtcc      1860
caccgggacc ccggggacaa caccacccc cagcccggc ggtggcgtcg ggggagccgc      1920
```

-continued

```
ctggaggagt cgtctcaact ccatccgcaa cagcttcctg ggctcccctc gctttcaccg    1980
gcgcaagatg caggtcccta ccgctgagga gatgtccagc ttgacgccag agtcctcccc    2040
ggagctggca aaacgctcct ggttcgggaa cttcatctcc ttggacaaag aagaacaaat    2100
attcctcgtg ctaaaggaca aacctctcag cagcatcaaa gcagacatcg tccatgcctt    2160
tctgtcgatc cccagcctga gtcacagtgt gctgtcacag accagcttca gggccgagta    2220
caaggccagt ggcggcccct ccgtcttcca aaagcccgtc cgcttccagg tggacatcag    2280
ctcctctgag gtccagagcc ctccccgcg acgggacggc agcggaggtg gtggcatcta    2340
ctccgtcacc ttcactctca tctcgggtcc cagccgtcgg ttcaagcgag tggtggagac    2400
catccaggca cagctcctga gcactcatga ccagccctcc gtgcaggccc tggcagacga    2460
gaagaacggg gcccagaccc ggcctgctgg tgccccaccc cgaagcctgc agcccccacc    2520
cggccgccca gacccagagc tgagcagctc tccccgccga ggccccccca aggacaagaa    2580
gctcctggcc accaacggga cccctctgcc ctgaccccac ggggccgggg agggagggga    2640
cccccctcca cccccttcc gtgccccca actgtgaatc tgtaaataag cccaaggaa     2700
catgtcggga gggggtgga cacaaaaacc ggccttgccc tgcagggatg gggctccaca    2760
ggccgtgccc aactgggggt ggttctaggg aacaggggg cggggagct gtttctattt     2820
tatttattga ttaatttatt attttattta ttgatcaatc tctctgcggg gtggggtggg    2880
ggagggacgg gagctggttg gggtggctta gcagatccgg acagggccct ctgtccctgt    2940
gtcgtcccca accccctctt cccgggcccc tcctcccctg gtcctccccc cacgaccttc    3000
tgtacggatt tgctctccgg aaggaattct ggtttcgcgt gatcctgcct gcgtccgtgt    3060
ctctgattcc gccggcggca aaaaaaaaaa aaaaaaaaa aaaaaaaaa             3109
```

<210> SEQ ID NO 4
<211> LENGTH: 778
<212> TYPE: PRT
<213> ORGANISM: Homo sapiens

<400> SEQUENCE: 4

```
Met Ser Ser Gly Ala Lys Glu Gly Gly Gly Ser Pro Ala Tyr His
1               5                   10                  15

Leu Pro His Pro His Pro His Pro Pro Gln His Ala Gln Tyr Val Gly
                20                  25                  30

Pro Tyr Arg Leu Glu Lys Thr Leu Gly Lys Gly Gln Thr Gly Leu Val
            35                  40                  45

Lys Leu Gly Val His Cys Ile Thr Gly Gln Lys Val Ala Ile Lys Ile
        50                  55                  60

Val Asn Arg Glu Lys Leu Ser Glu Ser Val Leu Met Lys Val Glu Arg
65                  70                  75                  80

Glu Ile Ala Ile Leu Lys Leu Ile Glu His Pro His Val Leu Lys Leu
                85                  90                  95

His Asp Val Tyr Glu Asn Lys Lys Tyr Leu Tyr Leu Val Leu Glu His
                100                 105                 110

Val Ser Gly Gly Glu Leu Phe Asp Tyr Leu Val Lys Lys Gly Arg Leu
            115                 120                 125

Thr Pro Lys Glu Ala Arg Lys Phe Phe Arg Gln Ile Val Ser Ala Leu
        130                 135                 140

Asp Phe Cys His Ser Tyr Ser Ile Cys His Arg Asp Leu Lys Pro Glu
145                 150                 155                 160

Asn Leu Leu Leu Asp Glu Lys Asn Asn Ile Arg Ile Ala Asp Phe Gly
```

```
                        165                 170                 175
        Met Ala Ser Leu Gln Val Gly Asp Ser Leu Leu Glu Thr Ser Cys Gly
                        180                 185                 190

Ser Pro His Tyr Ala Cys Pro Glu Val Ile Lys Gly Glu Lys Tyr Asp
                        195                 200                 205

Gly Arg Arg Ala Asp Met Trp Ser Cys Gly Val Ile Leu Phe Ala Leu
                        210                 215                 220

Leu Val Gly Ala Leu Pro Phe Asp Asp Asp Asn Leu Arg Gln Leu Leu
        225                 230                 235                 240

Glu Lys Val Lys Arg Gly Val Phe His Met Pro His Phe Ile Pro Pro
                        245                 250                 255

Asp Cys Gln Ser Leu Leu Arg Gly Met Ile Glu Val Glu Pro Glu Lys
                        260                 265                 270

Arg Leu Ser Leu Glu Gln Ile Gln Lys His Pro Trp Tyr Leu Gly Gly
                        275                 280                 285

Lys His Glu Pro Asp Pro Cys Leu Glu Pro Ala Pro Gly Arg Arg Val
                        290                 295                 300

Ala Met Arg Ser Leu Pro Ser Asn Gly Glu Leu Asp Pro Asp Val Leu
        305                 310                 315                 320

Glu Ser Met Ala Ser Leu Gly Cys Phe Arg Asp Arg Glu Arg Leu His
                        325                 330                 335

Arg Glu Leu Arg Ser Glu Glu Asn Gln Glu Lys Met Ile Tyr Tyr
                        340                 345                 350

Leu Leu Leu Asp Arg Lys Glu Arg Tyr Pro Ser Cys Glu Asp Gln Asp
                        355                 360                 365

Leu Pro Pro Arg Asn Asp Val Asp Pro Pro Arg Lys Arg Val Asp Ser
        370                 375                 380

Pro Met Leu Ser Arg His Gly Lys Arg Arg Pro Glu Arg Lys Ser Met
        385                 390                 395                 400

Glu Val Leu Ser Ile Thr Asp Ala Gly Gly Gly Ser Pro Val Pro
                        405                 410                 415

Thr Arg Arg Ala Leu Glu Met Ala Gln His Ser Gln Arg Ser Arg Ser
                        420                 425                 430

Val Ser Gly Ala Ser Thr Gly Leu Ser Ser Ser Pro Leu Ser Ser Pro
                        435                 440                 445

Arg Ser Pro Val Phe Ser Phe Ser Pro Glu Pro Gly Ala Gly Asp Glu
                        450                 455                 460

Ala Arg Gly Gly Gly Ser Pro Thr Ser Lys Thr Gln Thr Leu Pro Ser
        465                 470                 475                 480

Arg Gly Pro Arg Gly Gly Ala Gly Glu Gln Pro Pro Pro Ser
                        485                 490                 495

Ala Arg Ser Thr Pro Leu Pro Gly Pro Pro Gly Ser Pro Arg Ser Ser
                        500                 505                 510

Gly Gly Thr Pro Leu His Ser Pro Leu His Thr Pro Arg Ala Ser Pro
                        515                 520                 525

Thr Gly Thr Pro Gly Thr Thr Pro Pro Ser Pro Gly Gly Gly Val
                        530                 535                 540

Gly Gly Ala Ala Trp Arg Ser Arg Leu Asn Ser Ile Arg Asn Ser Phe
        545                 550                 555                 560

Leu Gly Ser Pro Arg Phe His Arg Arg Lys Met Gln Val Pro Thr Ala
                        565                 570                 575

Glu Glu Met Ser Ser Leu Thr Pro Glu Ser Ser Pro Glu Leu Ala Lys
                        580                 585                 590
```

-continued

```
Arg Ser Trp Phe Gly Asn Phe Ile Ser Leu Asp Lys Glu Glu Gln Ile
    595                 600                 605
Phe Leu Val Leu Lys Asp Lys Pro Leu Ser Ser Ile Lys Ala Asp Ile
    610                 615                 620
Val His Ala Phe Leu Ser Ile Pro Ser Leu Ser His Ser Val Leu Ser
625                 630                 635                 640
Gln Thr Ser Phe Arg Ala Glu Tyr Lys Ala Ser Gly Gly Pro Ser Val
                645                 650                 655
Phe Gln Lys Pro Val Arg Phe Gln Val Asp Ile Ser Ser Ser Glu Gly
                660                 665                 670
Pro Glu Pro Ser Pro Arg Arg Asp Gly Ser Gly Gly Gly Ile Tyr
                675                 680                 685
Ser Val Thr Phe Thr Leu Ile Ser Gly Pro Ser Arg Arg Phe Lys Arg
    690                 695                 700
Val Val Glu Thr Ile Gln Ala Gln Leu Leu Ser Thr His Asp Gln Pro
705                 710                 715                 720
Ser Val Gln Ala Leu Ala Asp Glu Lys Asn Gly Ala Gln Thr Arg Pro
                725                 730                 735
Ala Gly Ala Pro Pro Arg Ser Leu Gln Pro Pro Gly Arg Pro Asp
                740                 745                 750
Pro Glu Leu Ser Ser Ser Pro Arg Arg Gly Pro Pro Lys Asp Lys Lys
    755                 760                 765
Leu Leu Ala Thr Asn Gly Thr Pro Leu Pro
    770                 775

<210> SEQ ID NO 5
<211> LENGTH: 3576
<212> TYPE: DNA
<213> ORGANISM: Homo sapiens

<400> SEQUENCE: 5
agtctcaggc tggctagttc ctccttcctg gtcactgagc cagccttgct gaggggagag    60
cgggttctgg acgtgctctg agcttccttc ctcacagcct tgctcctggg ccagatcagc   120
aggaaagcag ccagtgcccc gccatggcct gcccgggtgg ggtcctgaag ctggggccgg   180
agcaggggc acagttctgc cccatctggc cctagtttgg ggagggagcc tggtagggca   240
ccagcctcac cccatgagcc ctgagggcca ccccagccga tgggcacgtc cccgccggcc   300
ctgcatctgt ccttcctccc tctgctcccc aagagagccc aggtctggcc cagcggtggg   360
caggggaggg gccgcacatc acagagtgcc agctggccac actcccggcc acagctgct   420
ccagccgcac ctccaccttc ctcaaggcca gacctggctc tgcctgcagc ccagcccagc   480
aggtctggtg aagctggggg ttcactgcgt cacctgccag aaggtggcca tcaagatcgt   540
caaccgtgag aagctcagcg agtcggtgct gatgaaggtg gagcgggaga tcgcgatcct   600
gaagctcatt gagcaccccc acgtcctaaa gctcacgac gtttatgaaa acaaaaaata   660
tttgtacctg gtgctagaac acgtgtcagg tggtgagctc ttcgactacc tggtgaagaa   720
ggggaggctg acgcctaagg aggctcggaa gttcttccgg cagatcatct ctgcgctgga   780
cttctgccac agccactcca tatgccacag ggatctgaaa cctgaaaacc tcctgctgga   840
cgagaagaac aacatccgca tcgcagactt tggcatggcg tccctgcagg ttggcgacag   900
cctgttggag accagctgtg gtccccccca ctacgcctgc cccgaggtga tccgggggga   960
gaagtatgac ggccggaagg cggacgtgtg gagctgcggc gtcatcctgt tcgccttgct  1020
ggtgggggct ctgcccttcg acgatgacaa cttgcgacag ctgctggaga aggtgaagcg  1080
```

```
gggcgtgttc cacatgccgc actttatccc gcccgactgc cagagtctgc tacggggcat    1140
gatcgaggtg gacgccgcac gccgcctcac gctagagcac attcagaaac acatatggta    1200
tatagggggc aagaatgagc ccgaaccaga gcagcccatt cctcgcaagg tgcagatccg    1260
ctcgctgccc agcctggagg acatcgaccc cgacgtgctg gacagcatgc actcactggg    1320
ctgcttccga gaccgcaaca agctgctgca ggacctgctg tccgaggagg agaaccagga    1380
gaagatgatt tacttcctcc tcctggaccg gaaagaaagg tacccgagcc aggaggatga    1440
ggacctgccc ccccggaacg agatagaccc tccccggaag cgtgtggact ccccgatgct    1500
gaaccggcac ggcaagcggc ggccagaacg caaatccatg gaggtgctca gcgtgacgga    1560
cggcggctcc ccggtgcctg cgcggcgggc cattgagatg gcccagcacg ccagaggtc    1620 tcggtccatc agcggtgcct cctcaggcct ttccaccagc ccactcagca gcccccgggt    1680 gaccccctcac ccctcaccaa ggggcagtcc cctccccacc cccaagggga cacctgtcca    1740
cacgccaaag gagagcccgg ctggcacgcc caaccccacg ccccgtcca gccccagcgt    1800 cggagggtg ccctggaggg cgcggctcaa ctccatcaag aacagctttc tgggctcacc    1860
ccgcttccac cgccggaaac tgcaagttcc gacgccggag gagatgtcca acctgacacc    1920
agagtcgtcc ccagagctgg cgaagaagtc ctggtttggg aacttcatca gcctggagaa    1980
ggaggagcag atcttcgtgg tcatcaaaga caaacctctg agctccatca aggctgacat    2040
cgtgcacgcc ttcctgtcga ttcccagtct cagccacagc gtcatctccc aaacgagctt    2100
ccgggccgag tacaaggcca cggggggggcc agccgtgttc cagaagccgg tcaagttcca    2160
ggttgatatc acctacacgg agggtgggga ggcgcagaag gagaacggca tctactccgt    2220
caccttcacc ctgctctcag gccccagccg tcgcttcaag agggtggtgg agaccatcca    2280
ggcccagctg ctgagcacac acgacccgcc tgcggcccag cacttgtcag acaccactaa    2340
ctgtatggaa atgatgacgg ggcggctttc caaatgtgac gagaagaacg ggcaggcggc    2400
ccaggccccc agcacgcccg ccaagcggag tgcccacggc ccactcggtg actccgcggc    2460
cgctggccct ggccccggag gggacgccga gtacccaacg ggcaaggaca cggccaagat    2520
gggccccgcc accgccgcc gcgagcagcc ttagacacac tagccccccc cccagcaca    2580 gcactgacag cggctgcctc gccgcccgcc gcccgccctg ccccgagtgg accgcggcc    2640 gcgccgcccg tccgtccaga ctgttctcag agcctgggag gaaaggaaag gggcgttggg    2700
gccggcctgt gggctgcgcc acccgcgccc gctctctttt ctctctgtct ctgcctctgc    2760
ctgtctctga cagcatcgct tgtttccact ctgataccag gaattatccc gaaaagttaa    2820
catgtcacct ccacgaggcc atcctctgtg accgaaggca gctgctgcgg acccgccctc    2880
cctccgctcc tgctgttgct gccgggcagt gaggcccagc ccagcgcccc gtccacccg    2940 cggcagctcc tcgcctcagc tccgcacggc ccgtgggagg aaggccaggc tcggggagc    3000 ctcctccagc ccgccgacc cggactcccg gtcacctgac ccctcagcaa gaacagcctg    3060
cctggtggcc ttctgggggcc aggacccctg gtgggcaacg tagccacagg aacaggcccc    3120
gtccaccgcc tccacgccgc acctggaggc ctcctcgcag gcccgtgccc cgcctccctg    3180
gccgcgccgc ctccgtgtag tcttggcctc ctcaggctgc ctcccgtcct ctcgtctcac    3240
ccgcgcctcc cttgcctcat ctggggcggc tgtgggctct ggcgctcctc tctggctgag    3300
gtggaaacag agacaccctg cggcaccaga gccttccag caggccaggc cgctgggctg    3360
ggatcagtgt tatttatttg ccgttttaat ttatggattc tccgcacctc tgttcaggga    3420
agggcggcgg ccacatcccc tgccgtctgc gtgtctcagg cagtgggggg gctgggggcca    3480
```

```
gggcgccctc tgaggacaga gctggtgggg cgcgggggggg ctggcgagct actgtaaact    3540
ttaaagaatt cctgcaagat atttttataa actttt                              3576
```

<210> SEQ ID NO 6
<211> LENGTH: 766
<212> TYPE: PRT
<213> ORGANISM: Homo sapiens

<400> SEQUENCE: 6

```
Met Ser Pro Glu Gly His Pro Ser Arg Trp Ala Arg Pro Arg Pro
1               5                   10                  15

Cys Ile Cys Pro Ser Ser Leu Cys Ser Pro Arg Glu Pro Arg Ser Gly
            20                  25                  30

Pro Ala Val Gly Arg Gly Gly Ala Ala His His Arg Val Pro Ala Gly
            35                  40                  45

His Thr Pro Gly Pro Gln Leu Leu Gln Pro His Leu His Leu Pro Gln
        50                  55                  60

Gly Gln Thr Trp Leu Cys Leu Gln Pro Ser Pro Ala Gly Leu Val Lys
65                  70                  75                  80

Leu Gly Val His Cys Val Thr Cys Gln Lys Val Ala Ile Lys Ile Val
                85                  90                  95

Asn Arg Glu Lys Leu Ser Glu Ser Val Leu Met Lys Val Glu Arg Glu
            100                 105                 110

Ile Ala Ile Leu Lys Leu Ile Glu His Pro His Val Leu Lys Leu His
            115                 120                 125

Asp Val Tyr Glu Asn Lys Lys Tyr Leu Tyr Leu Val Leu Glu His Val
        130                 135                 140

Ser Gly Gly Glu Leu Phe Asp Tyr Leu Val Lys Lys Gly Arg Leu Thr
145                 150                 155                 160

Pro Lys Glu Ala Arg Lys Phe Phe Arg Gln Ile Ile Ser Ala Leu Asp
                165                 170                 175

Phe Cys His Ser His Ser Ile Cys His Arg Asp Leu Lys Pro Glu Asn
            180                 185                 190

Leu Leu Leu Asp Glu Lys Asn Asn Ile Arg Ile Ala Asp Phe Gly Met
            195                 200                 205

Ala Ser Leu Gln Val Gly Asp Ser Leu Leu Glu Thr Ser Cys Gly Ser
        210                 215                 220

Pro His Tyr Ala Cys Pro Glu Val Ile Arg Gly Glu Lys Tyr Asp Gly
225                 230                 235                 240

Arg Lys Ala Asp Val Trp Ser Cys Gly Val Ile Leu Phe Ala Leu Leu
                245                 250                 255

Val Gly Ala Leu Pro Phe Asp Asp Asp Asn Leu Arg Gln Leu Leu Glu
            260                 265                 270

Lys Val Lys Arg Gly Val Phe His Met Pro His Phe Ile Pro Pro Asp
            275                 280                 285

Cys Gln Ser Leu Leu Arg Gly Met Ile Glu Val Asp Ala Ala Arg Arg
        290                 295                 300

Leu Thr Leu Glu His Ile Gln Lys His Ile Trp Tyr Ile Gly Gly Lys
305                 310                 315                 320

Asn Glu Pro Glu Pro Glu Gln Pro Ile Pro Arg Lys Val Gln Ile Arg
                325                 330                 335

Ser Leu Pro Ser Leu Glu Asp Ile Asp Pro Asp Val Leu Asp Ser Met
            340                 345                 350

His Ser Leu Gly Cys Phe Arg Asp Arg Asn Lys Leu Leu Gln Asp Leu
        355                 360                 365
```

Leu Ser Glu Glu Glu Asn Gln Glu Lys Met Ile Tyr Phe Leu Leu Leu
        370                 375                 380

Asp Arg Lys Glu Arg Tyr Pro Ser Gln Glu Asp Glu Asp Leu Pro Pro
385                 390                 395                 400

Arg Asn Glu Ile Asp Pro Pro Arg Lys Arg Val Asp Ser Pro Met Leu
                405                 410                 415

Asn Arg His Gly Lys Arg Arg Pro Glu Arg Lys Ser Met Glu Val Leu
            420                 425                 430

Ser Val Thr Asp Gly Gly Ser Pro Val Pro Ala Arg Arg Ala Ile Glu
        435                 440                 445

Met Ala Gln His Gly Gln Arg Ser Arg Ser Ile Ser Gly Ala Ser Ser
    450                 455                 460

Gly Leu Ser Thr Ser Pro Leu Ser Ser Pro Arg Val Thr Pro His Pro
465                 470                 475                 480

Ser Pro Arg Gly Ser Pro Leu Pro Thr Pro Lys Gly Thr Pro Val His
                485                 490                 495

Thr Pro Lys Glu Ser Pro Ala Gly Thr Pro Asn Pro Thr Pro Pro Ser
            500                 505                 510

Ser Pro Ser Val Gly Gly Val Pro Trp Arg Ala Arg Leu Asn Ser Ile
        515                 520                 525

Lys Asn Ser Phe Leu Gly Ser Pro Arg Phe His Arg Arg Lys Leu Gln
    530                 535                 540

Val Pro Thr Pro Glu Glu Met Ser Asn Leu Thr Pro Glu Ser Ser Pro
545                 550                 555                 560

Glu Leu Ala Lys Lys Ser Trp Phe Gly Asn Phe Ile Ser Leu Glu Lys
                565                 570                 575

Glu Glu Gln Ile Phe Val Val Ile Lys Asp Lys Pro Leu Ser Ser Ile
            580                 585                 590

Lys Ala Asp Ile Val His Ala Phe Leu Ser Ile Pro Ser Leu Ser His
        595                 600                 605

Ser Val Ile Ser Gln Thr Ser Phe Arg Ala Glu Tyr Lys Ala Thr Gly
    610                 615                 620

Gly Pro Ala Val Phe Gln Lys Pro Val Lys Phe Gln Val Asp Ile Thr
625                 630                 635                 640

Tyr Thr Glu Gly Gly Glu Ala Gln Lys Glu Asn Gly Ile Tyr Ser Val
                645                 650                 655

Thr Phe Thr Leu Leu Ser Gly Pro Ser Arg Arg Phe Lys Arg Val Val
            660                 665                 670

Glu Thr Ile Gln Ala Gln Leu Leu Ser Thr His Asp Pro Pro Ala Ala
        675                 680                 685

Gln His Leu Ser Asp Thr Thr Asn Cys Met Glu Met Met Thr Gly Arg
    690                 695                 700

Leu Ser Lys Cys Asp Glu Lys Asn Gly Gln Ala Ala Gln Ala Pro Ser
705                 710                 715                 720

Thr Pro Ala Lys Arg Ser Ala His Gly Pro Leu Gly Asp Ser Ala Ala
                725                 730                 735

Ala Gly Pro Gly Pro Gly Gly Asp Ala Glu Tyr Pro Thr Gly Lys Asp
            740                 745                 750

Thr Ala Lys Met Gly Pro Pro Thr Ala Arg Arg Glu Gln Pro
        755                 760                 765

<210> SEQ ID NO 7
<211> LENGTH: 23
<212> TYPE: DNA

```
<213> ORGANISM: Artificial Sequence
<220> FEATURE:
<223> OTHER INFORMATION: DNA primer

<400> SEQUENCE: 7
cgatgacatc gacggggaag gac                                         23

<210> SEQ ID NO 8
<211> LENGTH: 23
<212> TYPE: DNA
<213> ORGANISM: Artificial Sequence
<220> FEATURE:
<223> OTHER INFORMATION: DNA primer

<400> SEQUENCE: 8
gatggcctcg tggaggtgac atg                                         23

<210> SEQ ID NO 9
<211> LENGTH: 57
<212> TYPE: DNA
<213> ORGANISM: Artificial Sequence
<220> FEATURE:
<223> OTHER INFORMATION: DNA primer

<400> SEQUENCE: 9
gccaccatgg attacaagga tgacgacgat aagacatcga cggggaagga cggcggc    57

<210> SEQ ID NO 10
<211> LENGTH: 23
<212> TYPE: DNA
<213> ORGANISM: Artificial Sequence
<220> FEATURE:
<223> OTHER INFORMATION: DNA primer

<400> SEQUENCE: 10
gatggcctcg tggaggtgac atg                                         23

<210> SEQ ID NO 11
<211> LENGTH: 34
<212> TYPE: DNA
<213> ORGANISM: Artificial Sequence
<220> FEATURE:
<223> OTHER INFORMATION: DNA primer

<400> SEQUENCE: 11
ccagaaggtg gccatcatga tcgtcaaccg tgag                             34

<210> SEQ ID NO 12
<211> LENGTH: 34
<212> TYPE: DNA
<213> ORGANISM: Artificial Sequence
<220> FEATURE:
<223> OTHER INFORMATION: DNA primer

<400> SEQUENCE: 12
cgccgcacgc cgcctcgcgc tagagcacat tcag                             34

<210> SEQ ID NO 13
<211> LENGTH: 20
<212> TYPE: DNA
<213> ORGANISM: Artificial Sequence
<220> FEATURE:
<223> OTHER INFORMATION: DNA primer

<400> SEQUENCE: 13
gtcacctgac ccctcagcaa                                             20
```

```
<210> SEQ ID NO 14
<211> LENGTH: 20
<212> TYPE: DNA
<213> ORGANISM: Artificial Sequence
<220> FEATURE:
<223> OTHER INFORMATION: DNA primer

<400> SEQUENCE: 14
caccagctct gtcctcagag                                                 20

<210> SEQ ID NO 15
<211> LENGTH: 13
<212> TYPE: PRT
<213> ORGANISM: Artificial Sequence
<220> FEATURE:
<223> OTHER INFORMATION: enzyme substrate

<400> SEQUENCE: 15

Lys Lys Leu Asn Arg Thr Leu Ser Phe Ala Glu Pro Gly
1               5                   10

<210> SEQ ID NO 16
<211> LENGTH: 21
<212> TYPE: DNA
<213> ORGANISM: Mus musculus

<400> SEQUENCE: 16
agcgagagat tgccatcttg a                                               21

<210> SEQ ID NO 17
<211> LENGTH: 21
<212> TYPE: DNA
<213> ORGANISM: Mus musculus

<400> SEQUENCE: 17
gccagagaac ctgctgttgg a                                               21

<210> SEQ ID NO 18
<211> LENGTH: 3117
<212> TYPE: DNA
<213> ORGANISM: Homo sapiens

<400> SEQUENCE: 18
tgttcggctc agctgcacgg ctcggctcgg ctcggctcgg ctcggctgcg cggccgctga     60
cgggcgtgcg ctgggggcgc ggggcgcggg gcgcgggcct cggcggcggc ggcggcggcg    120
gcggcggaag ccaggtgccc ccgcccgccc tgtcctctcg acgaggcgga ggcgtcgccg    180
cgggccaggc ctcggactgc cgcgtcggag tggacgcggg gggcggcggc gcgggcggac    240
gcgggcggcg cgaagcagcg gggcccgcgg gggcgccccg gccgggtcgg cgcggacggc    300
actcggcgga cgcgggcgga cgctgggcgg ccccctccctg cccgcgcgcc cgggcgcccc    360
tggccggcgc tgggccccag agcgatgaca tcgacgggga aggacggcgg cgcgcagcac    420
gcgcagtatg ttgggcccta ccggctggag aagacgctgg gcaagggcca gacaggtctg    480
gtgaagctgg gggttcactg cgtcacctgc cagaaggtgg ccatcaagat cgtcaaccgt    540
gagaagctca gcgagtcggt gctgatgaag gtggagcggg agatcgcgat cctgaagctc    600
attgagcacc cccacgtcct aaagctgcac gacgtttatg aaaacaaaaa atatttgtac    660
ctggtgctag aacacgtgtc aggtggtgag ctcttcgact acctggtgaa gaaggggagg    720
ctgacgccta aggaggctcg gaagttcttc cggcagatca tctctgcgct ggacttctgc    780
cacagccact ccatatgcca cagggatctg aaacctgaaa acctcctgct ggacgagaag    840
```

```
aacaacatcc gcatcgcaga ctttggcatg gcgtccctgc aggttggcga cagcctgttg    900
gagaccagct gtgggtcccc ccactacgcc tgccccgagg tgatccgggg ggagaagtat    960
gacggccgga aggcggacgt gtggagctgc ggcgtcatcc tgttcgcctt gctggtgggg   1020
gctctgccct tcgacgatga caacttgcga cagctgctgg agaaggtgaa gcggggcgtg   1080
ttccacatgc cgcactttat cccgcccgac tgccagagtc tgctacgggg catgagcgag   1140
gtggacgccg cacgccgcct cacgctagag cacattcaga aacacatatg gtatataggg   1200
ggcaagaatg agcccgaacc agagcagccc attcctcgca aggtgcagat ccgctcgctg   1260
cccagcctgg aggacatcga ccccgacgtg ctggacagca tgcactcact gggctgcttc   1320
cgagaccgca acaagctgct gcaggacctg ctgtccgagg aggagaacca ggagaagatg   1380
atttacttcc tcctcctgga ccggaaagaa aggtacccga gccaggagga tgaggacctg   1440
cccccccgga acgagataga ccctccccgg aagcgtgtgg actccccgat gctgaaccgg   1500
cacggcaagc ggcggccaga acgcaaatcc atggaggtgc tcagcgtgac ggacggcggc   1560
tccccggtgc ctgcgcggcg ggccattgag atggcccagc acggccagag gtctcggtcc   1620
atcagcggtg cctcctcagg cctttccacc agcccactca gcagccccg gtgacccct    1680 caccccctcac caaggggcag tcccctcccc accccaagg ggacacctgt ccacacgcca    1740
aaggagagcc cggctggcac gcccaacccc acgccccgt ccagcccag cgtcggaggg    1800 gtgccctgga gggcgcggct caactccatc aagaacagct ttctgggctc accccgcttc   1860
caccgccgaa aactgcaagt tccgacgccg gaggagatgt ccaacctgac accagagtcg   1920
tccccagagc tggcgaagaa gtcctggttt ggaacttca tcagcctgga aaggaggag    1980 cagatcttcg tggtcatcaa agacaaacct ctgagctcca tcaaggctga catcgtgcac   2040
gccttcctgt cgattcccag tctcagccac agcgtcatct cccaaacgag cttccgggcc   2100
gagtacaagg ccacgggggg gccagccgtg ttccagaagc cggtcaagtt ccaggttgat   2160
atcacctaca cggagggtgg ggaggcgcag aaggagaacg gcatctactc cgtcaccttc   2220
accctgctct caggccccag ccgtcgcttc aagagggtgg tggagaccat ccaggcccag   2280
ctgctgagca cacgcgaccc gcctgcggcc cagcacttgt cagacaccac taactgtatg   2340
gaaatgatga cggggcggct ttccaaatgt ggaattatcc cgaaaagtta acatgtcacc   2400
tccacgaggc catcctctgt gaccgaaggc agctgctgcg gacccgccct ccctccgctc   2460
ctgctgttgc tgccgggcag tgaggcccag cccagcgccc cgtccacccc gcggcagctc   2520
ctcgcctcag ctccgcacgg cccgtgggag gaaggccagg ctcgggggag cctcctccag   2580
cccggccgac ccggactccc ggtcacctga cccctcagca gaacagcct gcctggtggc    2640 cttctggggc caggaccccc ggtgggcaac gtagccacag gaacaggccc cgtccaccgc   2700
ctccacgccg cacctggagg cctcctgcag gccgtgccc cgcctccctg gccgcgccgc    2760
ctccgtgtag tcttggcctc ctcaggctgc ctcccgtcct ctcgtctcac ccgcgcctcc   2820
cttgcctcat ctggggaggc tgtgggctct ggcgctcctc tctggctgag gtggaaacag   2880
agacaccctg cggcaccaga gccttcccag caggccaggc cgctgggctg ggatcagtgt   2940
tatttatttg ccgttttcca atttatggat tctccgcacc tctgttcagg aagggcggc     3000 ggccacatcc cctgccgtct gcgtgtctca ggcagtgggg gggctgggc cagggcgccc    3060 tctgaggaca gagctggtgg ggcgcggggg ggctggcgag ctactgtaaa ctttaaa      3117
```

<210> SEQ ID NO 19
<211> LENGTH: 668

```
<212> TYPE: PRT
<213> ORGANISM: Homo sapiens

<400> SEQUENCE: 19

Met Thr Ser Thr Gly Lys Asp Gly Gly Ala Gln His Ala Gln Tyr Val
1               5                   10                  15

Gly Pro Tyr Arg Leu Glu Lys Thr Leu Gly Lys Gly Gln Thr Gly Leu
            20                  25                  30

Val Lys Leu Gly Val His Cys Val Thr Cys Gln Lys Val Ala Ile Lys
        35                  40                  45

Ile Val Asn Arg Glu Lys Leu Ser Glu Ser Val Leu Met Lys Val Glu
50                  55                  60

Arg Glu Ile Ala Ile Leu Lys Leu Ile Glu His Pro His Val Leu Lys
65                  70                  75                  80

Leu His Asp Val Tyr Glu Asn Lys Lys Tyr Leu Tyr Leu Val Leu Glu
                85                  90                  95

His Val Ser Gly Gly Glu Leu Phe Asp Tyr Leu Val Lys Lys Gly Arg
            100                 105                 110

Leu Thr Pro Lys Glu Ala Arg Lys Phe Phe Arg Gln Ile Ile Ser Ala
        115                 120                 125

Leu Asp Phe Cys His Ser His Ser Ile Cys His Arg Asp Leu Lys Pro
130                 135                 140

Glu Asn Leu Leu Leu Asp Glu Lys Asn Asn Ile Arg Ile Ala Asp Phe
145                 150                 155                 160

Gly Met Ala Ser Leu Gln Val Gly Asp Ser Leu Leu Glu Thr Ser Cys
                165                 170                 175

Gly Ser Pro His Tyr Ala Cys Pro Glu Val Ile Arg Gly Glu Lys Tyr
            180                 185                 190

Asp Gly Arg Lys Ala Asp Val Trp Ser Cys Gly Val Ile Leu Phe Ala
        195                 200                 205

Leu Leu Val Gly Ala Leu Pro Phe Asp Asp Asn Leu Arg Gln Leu
210                 215                 220

Leu Glu Lys Val Lys Arg Gly Val Phe His Met Pro His Phe Ile Pro
225                 230                 235                 240

Pro Asp Cys Gln Ser Leu Leu Arg Gly Met Ser Glu Val Asp Ala Ala
                245                 250                 255

Arg Arg Leu Thr Leu Glu His Ile Gln Lys His Ile Trp Tyr Ile Gly
            260                 265                 270

Gly Lys Asn Glu Pro Glu Pro Glu Gln Pro Ile Pro Arg Lys Val Gln
        275                 280                 285

Ile Arg Ser Leu Pro Ser Leu Glu Asp Ile Asp Pro Asp Val Leu Asp
290                 295                 300

Ser Met His Ser Leu Gly Cys Phe Arg Asp Arg Asn Lys Leu Leu Gln
305                 310                 315                 320

Asp Leu Leu Ser Glu Glu Asn Gln Glu Lys Met Ile Tyr Phe Leu
                325                 330                 335

Leu Leu Asp Arg Lys Glu Arg Tyr Pro Ser Gln Glu Asp Glu Asp Leu
            340                 345                 350

Pro Pro Arg Asn Glu Ile Asp Pro Arg Lys Arg Val Asp Ser Pro
        355                 360                 365

Met Leu Asn Arg His Gly Lys Arg Arg Pro Glu Arg Lys Ser Met Glu
370                 375                 380

Val Leu Ser Val Thr Asp Gly Gly Ser Pro Val Pro Ala Arg Arg Ala
385                 390                 395                 400
```

```
                                    -continued
Ile Glu Met Ala Gln His Gly Gln Arg Ser Arg Ser Ile Ser Gly Ala
                    405                 410                 415

Ser Ser Gly Leu Ser Thr Ser Pro Leu Ser Ser Pro Arg Val Thr Pro
                420                 425                 430

His Pro Ser Pro Arg Gly Ser Pro Leu Pro Thr Pro Lys Gly Thr Pro
            435                 440                 445

Val His Thr Pro Lys Glu Ser Pro Ala Gly Thr Pro Asn Pro Thr Pro
        450                 455                 460

Pro Ser Ser Pro Ser Val Gly Gly Val Pro Trp Arg Ala Arg Leu Asn
465                 470                 475                 480

Ser Ile Lys Asn Ser Phe Leu Gly Ser Pro Arg Phe His Arg Arg Lys
                485                 490                 495

Leu Gln Val Pro Thr Pro Glu Glu Met Ser Asn Leu Thr Pro Glu Ser
                500                 505                 510

Ser Pro Glu Leu Ala Lys Lys Ser Trp Phe Gly Asn Phe Ile Ser Leu
            515                 520                 525

Glu Lys Glu Glu Gln Ile Phe Val Val Ile Lys Asp Lys Pro Leu Ser
            530                 535                 540

Ser Ile Lys Ala Asp Ile Val His Ala Phe Leu Ser Ile Pro Ser Leu
545                 550                 555                 560

Ser His Ser Val Ile Ser Gln Thr Ser Phe Arg Ala Glu Tyr Lys Ala
                565                 570                 575

Thr Gly Gly Pro Ala Val Phe Gln Lys Pro Val Lys Phe Gln Val Asp
                580                 585                 590

Ile Thr Tyr Thr Glu Gly Gly Glu Ala Gln Lys Glu Asn Gly Ile Tyr
            595                 600                 605

Ser Val Thr Phe Thr Leu Leu Ser Gly Pro Ser Arg Arg Phe Lys Arg
            610                 615                 620

Val Val Glu Thr Ile Gln Ala Gln Leu Leu Ser Thr His Asp Pro Pro
625                 630                 635                 640

Ala Ala Gln His Leu Ser Asp Thr Thr Asn Cys Met Glu Met Met Thr
                645                 650                 655

Gly Arg Leu Ser Lys Cys Gly Ile Ile Pro Lys Ser
                660                 665
```